US008975060B2

(12) United States Patent
Talebpour et al.

(10) Patent No.: US 8,975,060 B2
(45) Date of Patent: Mar. 10, 2015

(54) METHOD FOR PRETREATMENT OF MICROBIAL SAMPLES

(71) Applicant: Qvella Corporation, Richmond Hill (CA)

(72) Inventors: Samad Talebpour, Richmond Hill (CA); Aye Aye Khine, Thornhill (CA); Robert Maaskant, King City (CA); Tino Alavie, Thornhill (CA)

(73) Assignee: Qvella Corporation, Richmond Hill, ON (CA)

( * ) Notice: Subject to any disclaimer, the term of this patent is extended or adjusted under 35 U.S.C. 154(b) by 39 days.

(21) Appl. No.: 13/833,872

(22) Filed: Mar. 15, 2013

(65) Prior Publication Data

US 2014/0154687 A1    Jun. 5, 2014

Related U.S. Application Data

(60) Provisional application No. 61/731,809, filed on Nov. 30, 2012, provisional application No. 61/750,242, filed on Jan. 8, 2013.

(51) Int. Cl.
*C12N 1/00*    (2006.01)

(52) U.S. Cl.
USPC .......................................................... 435/243

(58) Field of Classification Search
CPC ........................................................ C12N 1/00
USPC ............................................................ 435/243
See application file for complete search history.

(56) References Cited

U.S. PATENT DOCUMENTS

| | | | |
|---|---|---|---|
| 3,883,425 | A | 5/1975 | Dorn |
| 4,131,512 | A | 12/1978 | Dorn |
| 4,164,449 | A | 8/1979 | Dorn et al. |
| 4,212,948 | A | 7/1980 | Dorn |
| 4,693,972 | A | 9/1987 | Mansour et al. |
| 5,070,014 | A | 12/1991 | Dorn |
| 5,108,927 | A | 4/1992 | Dorn |
| 5,501,960 | A | 3/1996 | Dorn |
| 6,803,208 | B2 | 10/2004 | Seaver et al. |
| 6,864,100 | B1 * | 3/2005 | Ribbe et al. .................. 436/178 |
| 2008/0234474 | A1 * | 9/2008 | Braman et al. ............... 536/25.3 |
| 2011/0061474 | A1 | 3/2011 | Page et al. |
| 2011/0294128 | A1 | 12/2011 | Peytavi et al. |
| 2012/0190040 | A1 | 7/2012 | Talebpour et al. |
| 2013/0171615 | A1 | 7/2013 | Van Meerbergen et al. |
| 2014/0004501 | A1 | 1/2014 | Talebpour et al. |

FOREIGN PATENT DOCUMENTS

WO    2008122002    10/2008

OTHER PUBLICATIONS

Koolman, J. and Roehm, K., Hi, "Color Atlas of Biochemistry", [online] 2005 The claimed invention is directed to a method combining DNAzyme technology with gold nanoparticles for detecting the presence of a biological target or a number of different biological targets of interest in a sample. [Retrieved on Feb. 3, 2014] <URL:http://www.google.com/url?sa=t&rct=j&q=&esrc=s&source=web&cd=3&ved=0CDQQFjAC&url=http%3A%2F%2Ffaculty.ksu.edu.sa%2F15218%2FMedical%2520Books%2FColor%2520Atlas%2520of%2520Biochemistry%25202nd%25202005%2520U9iuKcSVqAabm4LADg&usg=AFQjCNEZnuEGtO-25whxFxJJj5rK1bhVQ>.*
Tan J. et al. "Kinetically limited differential centrifugation as an inexpensive and readily available alternative to centrifugal elutriation", Biotechniques Aug. 2012, vol. 53/2 pp. 104-108.
Ammons D. et al. "An apparatus to control and automate the formation of continuous density gradients", Analytical Biochemistry May 2011 (May 2012), vol. 427 pp. 124-126.
Zelenin et al. "Bacteria isolation from whole blood for sepsis diagnosis", 15th International Conference on Miniaturization Systems for Chemistry and Life Sciences Oct. 2-6, 2011, Seattle, Washington, USA pp. 518-520 [ Retrieved on Mar. 5, 2014].
"Chapter 3 Centrifugation", Published 2007 [Retrieved on Feb. 3, 2014 (May 3, 2014)]. <URL: http://www.phys.sinica.edu.tw/TIGP-NANO/Course/2007_Spring/Clase%20Notes/AC_Chapter%203%20Centrifugatoin%200321.pdf>.
Wampole Isolator Tube 7.4.5, www.asmpress.org/index.asp?downloadid=287, (2013).
Waleed Abu Al-Soud and Peter Radstrom, Purification and Characterization of PCR-Inhibitory Components in Blood Cells, Journal of Clinical Microbiology, (2001) 39:485-493.
David N. Fredricks and David A. Relman, Improved Amplification of Microbial DNA from Blood Cultures by Removal of the PCR Inhibitor Sodium Polyanetholesulfonate, Journal of Clinical Microbiology, (1998) 36:2810-2816.
Verne Schumaker and Allan Rees, Theory of Differential Centrifugation in Angle-Head Rotors, Analytical Biochemistry (1969) 31:279-285.
R. Phillip Dellinger et al., Surviving Sepsis Campaign: International guidelines for management of severe sepsis and septic shock: 2008, Intensive Care Med (2008) 34:17-60.
B. Arkles et al., Siliconization: Blood-Surface Interaction, Chemically Modified Surfaces vol. 1, Gordon and Breach Scientific Publishers, (1986).

(Continued)

*Primary Examiner* — Ardin Marschel
(74) *Attorney, Agent, or Firm* — Hill & Schumacher; Lynn C. Schumacher; Stephen W. Leonard

(57) ABSTRACT

Methods and devices are provided for pretreatment of a sample containing microbial cells. In some embodiments, the pretreatment of the sample is performed via the initial selective lysis, within a sample pretreatment vessel, of non-microbial cells (such as blood cells) and the subsequent centrifugation of the sample to remove the resulting debris and concentrate the microbial cells. An immiscible and dense cushioning liquid may be included, for collecting the microbial cells adjacent to a liquid interface formed by the cushioning liquid, upon centrifugation of the pretreatment vessel. After removal of a substantial quantity of the supernatant, resuspension of the collected microbial cells, and re-establishment of the liquid interface, at least a portion of the remaining suspension may be removed without substantially removing the cushioning liquid. One or more intermediate wash cycles may be performed to prior to extraction of the pretreated sample.

16 Claims, 36 Drawing Sheets

(56) References Cited

OTHER PUBLICATIONS

Peter Gilbert et al., Centrifugation injury of Gram-negative Bacteria, Journal of Antimicrobial Chemotherapy (1991) 27:550-551.
Wampole Isostat System, https://ensur.invmed.com/ensur/broker/ensurbroker.aspx, (2013).
Mathias Bernhardt et al., Detection of Bacteria in Blood by Centrifugation and Filtration, Journal of Clinical Microbiology, (1991) 29:422-425.
R. Blaine McCleskey, Electrical Conductivity of Electrolytes Found in Natural Waters from (5 to 90)° C., J. Chem. Eng. Data 2011, 56, 317-327.
Tan J. et al. "Kinetically limited differential centrifugation as an inexpensive and readily available alternative to centrifugal elutriation", Biotechniques Aug. 2012, vol. 5312 pp. 104-108.
Ruban S. W. et al. "Physical methods of separation and concentration of microbes in food: An aid for rapid detection", Journal of Food Technology 2011, vol. 9/3 pp. 106-111.
World Health Organization and Organisation of Economic Co-operation and Development, Assessing Microbial Safety of Drinking Water: Improving Approaches and Methods [online], IWA Publishing, Published 2003 [Retrieved on Feb. 3, 2014)]. <URL:http://www.who.int/water_sanitation_health/dwq/9241546301full.pdf.>.
Friberg A. S. et al. "Human islet separation utilizing a closed automated purification system", Cell Transplant 2008, vol. 17/12 pp. 1305-1313.
Ammons D. et al. "An apparatus to control and automate the formation of continuous density gradients", Analytical Biochemistry May 2011, vol. 427 pp. 124-126.
Lin L. et al. "Use of the sucrose gradient method for bacterial cell cycle syncronization", JMBE May 2012, vol. 13/1 pp. 50-53.
Zelenin et al. "Bacteria isolation from whole blood for sepsis diagnosis", 15th International Conference on Miniaturization Systems for Chemistry and Life Sciences Oct. 2-6, 2011, Seattle, Washington, USA pp. 518-520 [Retrieved on Mar. 5, 2014].
Gordon J. R. "Immunology methods manual, selected protocol—(Fractionation of cells by density gradient centrifugation)" [retrieved on Mar. 5, 2014]. <URL:http://homepage.usask.ca/~jrg426/manualrbclysis.html>.
"Chapter 3 Centrifugation", Published 2007 [Retrieved on Feb. 3, 2014]. <URL:http://www.phys.sinica.edu.tw/TIGP-NANO/Course/2007_Spring/Class%20Notes/AC_Chapter%203%20Centrifugatoin%200321.pdf>.
International Search Report for PCT application No. PCT/CA2013/000992, mailed Mar. 28, 2014.

\* cited by examiner

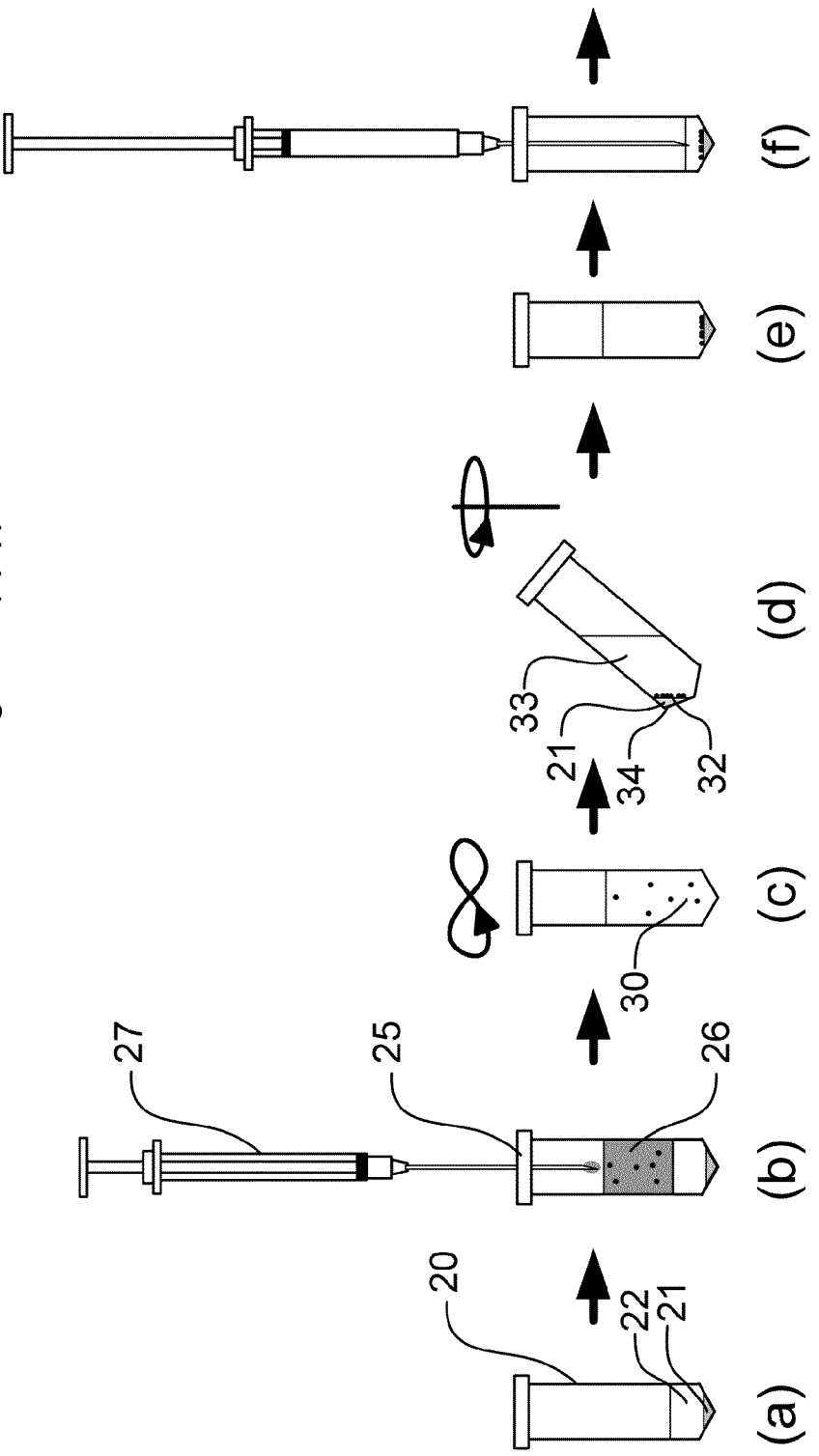
Figure 1 (a)-(f)

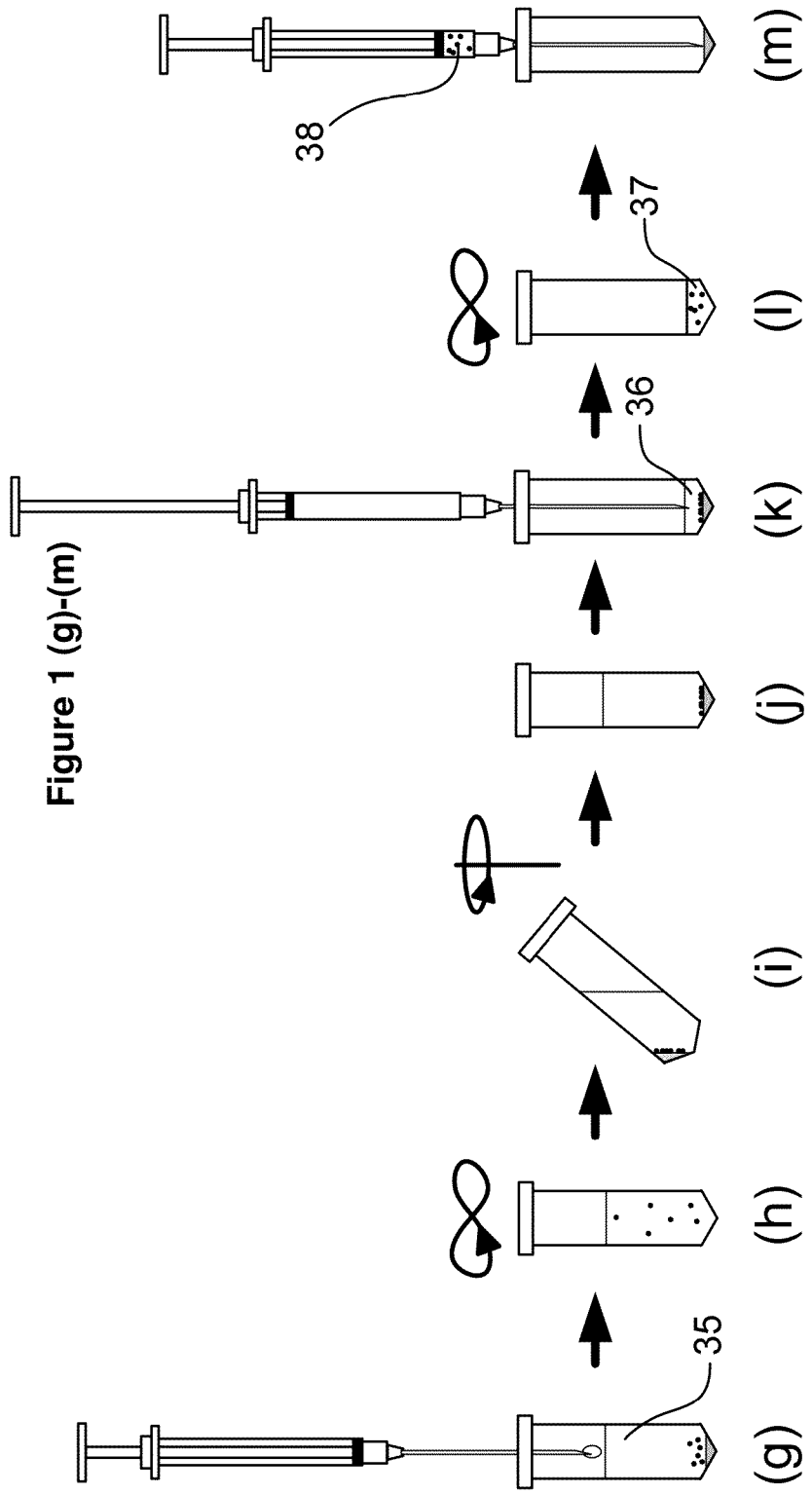

(ii)

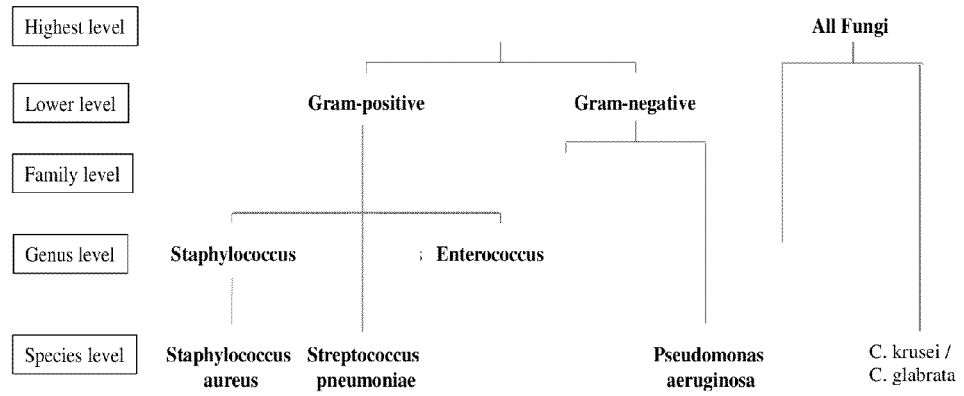

Figure 9(a)

| Case | Gram + | Gram - | Fungal | Staph. | Staph. aureus | Entero-coccus | Strep pneu. | Pseudo. aerug. | C. Kru. /Gla. | Organism | Example Antibiotic |
|---|---|---|---|---|---|---|---|---|---|---|---|
| 1 | ■ | | | ■ | ■ | | | | | Staph. aureus | Vanco + oxacillin |
| 2 | ■ | | | ■ | | | | | | Other Staph. | Suspect contaminant |
| 3 | ■ | | | | | | ■ | | | Strep. penu. | Vanco + ceftriaxone |
| 4 | ■ | | | | | ■ | | | | Enterrococcus | Vanco + ampicillin |
| 5 | ■ | | | | | | | | | Other Strep. | Ampicillin |
| 6 | | ■ | | | | | | | | Enterobacteria | Erapenem |
| 7 | | ■ | | | | | | ■ | | P. aeru. | Ceftizoxime |
| 8 | | | ■ | | | | | | | Other fungi | Fluconazole |
| 9 | | | ■ | | | | | | ■ | C. Krusei C. glabrata | Mycafungin |

Figure 9(b)

| Sample designation | Blood | Blood Treated | 3Wash | 3Wash Treated | 4Wash | 4Wash Treated | Buffer Control |
|---|---|---|---|---|---|---|---|
| $C_T$ (cycles) | 34.5 | 34 | 31 | 27 | 26 | 25 | 24 |

| C-albicans Samples/Controls | Fluorescence intensity |
|---|---|
| negative control; buffer | 94 |
| negative control; blood | 88 |
| 1 cell-positive control | 131 |
| 1 cell-spiked blood sample | 129 |
| 1 cell-spiked blood sample | 140 |
| 10 cells-positive control | 151 |
| 10 cell-spiked blood sample | 146 |

Figure 17

| S.pneumoniae Samples/Controls | Fluorescence intensity |
|---|---|
| negative control; buffer | 110 |
| negative control; blood | 112 |
| 1 cell-positive control | 159 |
| 1 cell-spiked blood sample | 126 |
| 1 cell-spiked blood sample | 142 |
| 10 cells-positive control | 177 |
| 10 cell-spiked blood sample | 134 |
| 10 cell-spiked blood sample | 165 |

Figure 19

| E.coli Samples/Controls | Fluorescence intensity |
|---|---|
| negative control; buffer | 113 |
| negative control; blood | 110 |
| 1 cell-positive control | 146 |
| 1 cell-spiked blood sample | 131 |
| 1 cell-spiked blood sample | 129 |
| 10 cells-positive control | 151 |
| 10 cell-spiked blood sample | 145 |
| 10 cell-spiked blood sample | 149 |

Figure 21

| Highest level | Lower level | Family level | Genus level | Species level | Microbial cells tested |
|---|---|---|---|---|---|
| All bacteria | Gram-positive | | Staphylococcus | Staphylococcus aureus | Staphylococcus aureus |
| | | | Streptococcus | Streptococcus pneumoniae | Streptococcus pneumoniae |
| | | | Other Streptococcus | | Streptococcus pyogenes Streptococcus sanguis |
| | | | Enterococcus | | Enterococcus faecalis |
| | Gram-negative | Enterobacteriacae | | | Escherichia coli Klebsiella pneumoniae Enterobacter cloacae Acinetobacter baumanni |
| | | | | Pseudomonas aeruginosa | Pseudomonas aeruginosa |
| All fungi | | | | | Candida albicans Candida glabrata Candida krusei Cryptococcus neoformans |
| | | | Aspergillus | | Aspergillus fumigatus |

Figure 22

| Target | Primer | Sequence | Amplicon size |
|---|---|---|---|
| Gram- Negative | GNF8 | 5'-GTTACCCGCAGAAGAAGCACCG-3' (SEQ ID NO: 23) | 151 |
| | GNR8 | 5'-ATGCAGTTCCCAGGTTGAGCC-3' (SEQ ID NO: 24) | |
| Gram- Positive | GPF8 | 5'-GCTCGTGTCGTGAGATGTTGGG-3' (SEQ ID NO: 21) | 151 |
| | GPR8 | 5'-CAGGTCATAAGGGGCATGATGAT-3' (SEQ ID NO: 22) | |
| Fungi | UFF2 | 5'- ACGGGGAGGTAGTGACAATAAAT-3' (SEQ ID NO: 9) | 190 |
| | UFR2 | 5'- CCCAAGGTTCAACTACGAGCTT-3' (SEQ ID NO: 10) | |

Figure 23

METHOD FOR PRETREATMENT OF MICROBIAL SAMPLES

CROSS-REFERENCE TO RELATED APPLICATION

This application claims priority to U.S. Provisional Application No. 61/731,809, titled "APPARATUS AND METHOD FOR PRE-TREATMENT OF MICROBIAL SAMPLES" and filed on Nov. 30, 2012, the entire contents of which is incorporated herein by reference, and to U.S. Provisional Application No. 61/750,242, titled "APPARATUS AND METHOD FOR PRE-TREATMENT OF MICROBIAL SAMPLES" and filed on Jan. 8, 2013, the entire contents of which is incorporated herein by reference.

BACKGROUND

This disclosure relates to methods of detecting the presence and the identity of microorganisms in a sample.

Emergence of drug resistant pathogens is a global healthcare crisis that is forcing physicians to treat common infectious diseases with ever more potent antibiotics. This is largely caused by the complexity and time required in identifying the offending bacteria, forcing physicians to prescribe empirically even with the knowledge of the high negativity rate amongst cultured specimens. The net result has been a significant increase in emergence of resistant strains, higher treatment costs, and longer recovery cycle due to an increase in side effect risks associated with taking broad spectrum and unnecessary antibiotics.

Broad spectrum antibiotics are commonly prescribed when treating patients that are exhibiting symptoms of sepsis or septic shock. Given the seriousness of these conditions, doctors will often prescribe one or more broad-spectrum antibiotics right away and are not likely to change the treatment regimen until the full effect of the drugs can be assessed or results from microbiology become available. For instance, the document "Surviving Sepsis Campaign Guideline" (SSCG) recommends a treatment protocol in which intravenous antibiotics, consisting of one or more broad-spectrum agents against likely bacterial/fungal pathogens, should be started within the first hour of recognizing severe sepsis and septic shock [R. P. Dellinger et al., Crit. Care Med 2008]. The treatment protocol states that the antimicrobial regimen is to be reassessed daily, and once the pathogen is known, as a matter of good practice, a more appropriate narrow-spectrum antimicrobial drug is to be administered.

Unfortunately, current clinical bacteriology methods typically provide pathogen identification information when it may be too late to impact patient outcomes. This is due to the time lag of 2-3 days from specimen collection to reporting results of pathogen identification and susceptibility testing. Causes for the time lag include the need to transport specimens to clinical laboratories staffed by expert clinical bacteriologists and the time required for blood culture and subsequent colony formation after plating the specimen on solid culture medium. Specimens that arrive at the clinical microbiology laboratory after normal business hours are typically held overnight until staff arrives the next day. Once specimens are plated on solid agar on day 2 (after a positive blood culture has been obtained), an additional 8-12 hours are needed for colonies to form. Plates are examined, colonies are enumerated, and appropriate colonies are selected for identification and susceptibility testing. The process further requires analysis and interpretation before reports are released, typically on day 3, which may be too slow to meaningfully impact antibiotic selection and patient outcomes.

While many aspects of clinical microbiology laboratory workflow have been automated, clinical bacteriology remains highly labour-intensive. Many laboratories currently automate identification and susceptibility testing using either the Vitek (Biomerieux) or Phoenix (Becton-Dickenson) instruments. However, these systems, and newer systems based on mass spectroscopy, depend on selection of appropriate colonies from overnight growth on agar plates by expert personnel.

Several nucleic acid amplification approaches for clinical bacteriology have recently been commercialized. However, most of these still require an nucleic acid extraction and purification step that can take more than 1 hour, as part of the pre-analytical process for species identification. These processes are required for providing an inhibitor and contaminant free sample for nucleic acid assays. Consequently, despite their specificity and sensitivity, molecular methods such as PCR have not replaced the much slower standard microbial culture-based techniques as the front line test in the clinical microbiology laboratory, and the results from clinical microbiology testing continue to be provided too late to substantially impact patient outcomes.

SUMMARY

Methods and devices are provided for pretreatment of a sample containing microbial cells. In some embodiments, the pretreatment of the sample is performed via the initial selective lysis, within a sample pretreatment vessel, of non-microbial cells (such as blood cells) and the subsequent centrifugation of the sample to remove the resulting debris and concentrate the microbial cells. An immiscible and dense cushioning liquid may be included, for collecting the microbial cells adjacent to the liquid interface formed by the sedimentation liquid, upon centrifugation of the pretreatment vessel. After removal of a substantial quantity of the supernatant, resuspension of the collected microbial cells, and re-establishment of the liquid interface, at least a portion of the remaining suspension may be removed without substantially removing the sedimentation liquid and the collected microbial cells. One or more intermediate wash cycles may be performed prior to extraction of the processed sample, which provides a "pretreated" sample Accordingly, in one aspect, there is provided a method of extracting microbial cells from a whole blood sample in a pretreatment vessel;
  the pretreatment vessel comprising a pretreatment mixture, the pretreatment mixture comprising:
    a blood cell lysis reagent; and
    a hydrophobic cushioning liquid having a density greater than that of the whole blood sample and the blood cell lysis reagent;
  the method comprising:
    adding a whole blood sample to the pretreatment vessel;
    agitating the contents of the pretreatment vessel;
    centrifuging the pretreatment vessel such that the cushioning liquid forms a liquid interface below a supernatant, wherein microbial cells within from the whole blood sample are removed from suspension and collected adjacent to the liquid interface;
    withdrawing a substantial quantity of the supernatant without extracting the collected microbial cells;

agitating the contents of the pretreatment vessel and allowing the cushioning liquid to re-establish the liquid interface below a suspension containing the microbial cells; and extracting a least a substantial portion of the suspension without extracting a substantial portion of the cushioning liquid.

In another aspect, there is provided a pretreatment vessel for extracting microbial cells from a whole blood sample, comprising:

a vessel body defining an internal volume and an enclosure mechanism for sealing the vessel, wherein the vessel body is configured for use in a centrifugation device, and wherein distal portion of the vessel body is conical in shape;

the vessel body containing:

a pretreatment mixture comprising a blood cell lysis reagent, and a hydrophobic cushioning liquid having a density greater than that of the whole blood sample and the blood cell lysis reagent, wherein the cushioning liquid forms a liquid interface below a supernatant upon centrifugation of the vessel body such that microbial cells within a whole blood sample are removed from suspension and collected adjacent to the liquid interface;

wherein the cushioning liquid has a volume between approximately 0.1% and 10% of the vessel volume.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 1 (a) to (m) depict the sample pretreatment vessel and its contents at different stages during sample pretreatment.

FIGS. 5 (a) and (b) schematically depicts example embodiment for automating the sample pretreatment method, while

FIG. 9(a) illustrates an example rapid identification panel for de-escalation of antibiotic therapy.

FIG. 9(b) illustrates example organism identification based on the results from the rapid identification panel shown in FIG. 8(a), with a corresponding example antibiotic selection.

FIG. 11 (b) shows the $C_T$ values for the plots in FIG. 10(a).

FIG. 17 is a table showing the fluorescence intensity values obtained for the detection of *Candida albicans* in blood samples detected by molecular beacon hybridization to reverse transcription PCR amplified 18S rRNA.

FIG. 19 is a table showing the fluorescence intensity values obtained for the detection of *Streptococcus pneumoniae* in blood samples detected by molecular beacon hybridization to reverse transcription PCR amplified 16S rRNA.

FIG. 21 is a table showing fluorescence intensity values for the detection of *Escherichia coli* in blood samples detected by molecular beacon hybridization to reverse transcription PCR amplified 16S rRNA.

FIG. 22 is a table describing the microbial cells that were tested.

FIG. 23 is a table describing the primers employed for RT-PCR.

DETAILED DESCRIPTION

Figure 2:
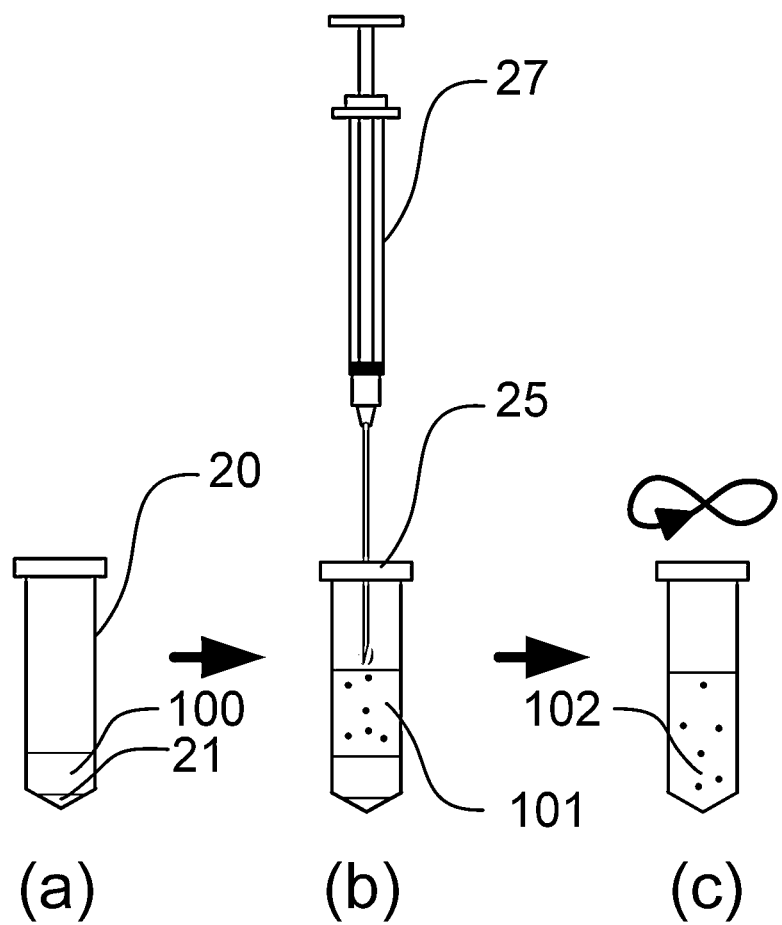
FIGS. 2(a)-(c) illustrate an alternative embodiment for performing pretreatment on a sample other than whole blood.

Various embodiments and aspects of the disclosure will be described with reference to details discussed below. The following description and drawings are illustrative of the disclosure and are not to be construed as limiting the disclosure.

Numerous specific details are described to provide a thorough understanding of various embodiments of the present disclosure. However, in certain instances, well-known or conventional details are not described in order to provide a concise discussion of embodiments of the present disclosure. It should be understood that the order of the steps of the methods disclosed herein is immaterial so long as the methods remain operable.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

In embodiments disclosed below, methods and devices are provided for sensitive detection and identification of microbial cells in a sample. In some embodiments, the pretreatment of the sample is performed via the initial selective lysis of non-microbial cells (such as blood cells) and the subsequent centrifugation of the sample to remove the resulting debris and concentrate the microbial cells. The resulting microbial cell suspension is termed herein as the pretreated sample.

Such a method was originally proposed by Dorn, for example, in U.S. Pat. Nos. 5,070,014, 4,131,512, 4,212,948, 4,693,972, and 5,108,927. Dorn teaches the use of a sample collection tube that includes saponin and a cushioning liquid, such as a high density liquid fluorinated hydrocarbon. A volume of whole blood is added to the sample collection tube, and the saponin lyses blood cells in the sample. The cushioning liquid forms a distinct liquid layer at the bottom of the sample collection tube, and is provided to collect microbial cells at its liquid interface when the tube is centrifuged and retain the viability of the microbial cells which may otherwise be damaged by impact or compaction forces in the resulting pellet. After removal of the majority of the supernatant, Dorn teaches the removal of all of the remaining liquid in the tube, including any residual supernatant and all of the cushioning liquid.

The method of Dorn enjoyed commercial success prior to the advent of automated blood culture systems, as it was suitable for preparing microbial cells in a form that could be readily cultured, while preserving the integrity of the concentrated microbial cells. Unfortunately, however, the present inventors have found that the Dorn sample preparation protocol is not suitable for many other applications, such as molecular assays.

Indeed, the requirement of the Dorn protocol that the final extracted sample include all of the cushioning liquid, and also a substantial quantity of the residual supernatant, can pose many problems, such as those leading to incompatibilities with downstream molecular methods due to the presence of inhibitory substances and contaminants. For example, in cases such as disclosed herein where the extracted cell suspension proceeds directly to lysis and a molecular assay without a subsequent extraction and purification step the transferred blood cell debris and the cushioning liquid may contribute significantly to inhibition and contamination of subsequent amplification of molecular targets. Moreover, the viability of the concentrated microbial cells and accordingly the impact and compaction protection offered by the cushioning liquid is not a requirement for molecular assay applications.

Accordingly, in some embodiments of the present disclosure, devices and methods are provided for the separation and concentration of microbial cells from a liquid sample, in which a cushioning liquid is employed to collect microbial cells during a centrifugation step, but without substantially transferring the cushioning liquid when extracting the pretreated sample. Furthermore, in some embodiments, one or more wash procedures are performed prior to extraction of the pretreated sample in order to reduce the concentration of lysed blood cell debris and other undesirable components and substances that may be present in the pretreated sample. The reduction in concentration of these substances in the pretreated sample may be beneficial in avoiding enzyme inhibition for molecular assays, reducing the presence of non-target macromolecules and preventing degradation of target macromolecules.

The retained microbial cells present in the pretreated sample may be lysed and optionally subjected to treatment processes (example treatment processes are described further below) for rendering the intracellular nucleic acid macromolecules (such as ribosomal RNA (rRNA) and DNA) available for subsequent molecular analysis. In some embodiments, subsequent amplification and detection steps may be employed for the identification of the microbial cells. For example, the amplification and detection steps may be performed directly on the pretreated and lysed sample without employing common nucleic acid extraction and purification techniques. In particular, lysing techniques which do not employ reagents that would otherwise interfere with amplification and detection (for example, lysing techniques such as electrical, thermal and mechanical lysis) may be employed in this context.

In some embodiments, in which the sample is a blood sample containing blood cells (such as red blood cells and white blood cells) in addition to potentially containing microbial cells, the sample may be pre-treated in order to lyse the blood cells.

FIGS. 1(a)-(m) illustrate an example implementation of a pretreatment device and method according to one embodiment of the present disclosure, which may be employed for the pretreatment of whole blood samples. Referring to FIG. 1(a), pretreatment vessel 20 is provided containing a volume of blood cell lysis reagent 22 and volume of cushioning liquid 21.

Pretreatment vessel 20 is a vessel suitable for centrifugation, such as a microcentrifuge tube. In some embodiments, the centrifuge tube has a conical bottom shape and a smooth inner surface, which minimises adsorption or trapping of microbial cells during centrifugation. In some embodiments, pretreatment vessel 20 includes an injectable closure member, such as pierceable stopper 25 (such as a rubber stopper), or another suitable sealing mechanism that may be evacuated such that an appropriate volume of sample is drawn when the pierceable stopper is pierced by the needle of syringe 27.

In some embodiments, pretreatment vessel 20 is employed to obtain a selected volume of blood from a previously filled blood tube, such as another blood collection tube. In some embodiments, pretreatment vessel 20 may be employed as a sample collection device. For example, pretreatment vessel 20 may include a pierceable stopper that is configured for use with a Vacutainer®-type needle and holder device.

Cushioning liquid 21 is a high density and water immiscible liquid that serves to form liquid surface 32 onto which the microorganisms settle during centrifugation. As shown in FIG. 1(*a*), cushioning liquid 21 has a density such that it settles at the bottom of pretreatment vessel 20 under the influence of gravity. It will be understood that the term "high density", as used herein with regard to cushioning liquid 21, means a density that is sufficiently high such that the target microbial cells will not substantially penetrate the cushioning liquid under the prevailing centrifugal force. The density of the cushioning liquid 21 is therefore chosen be greater than both the microbial cells and the other liquids. The cushioning liquid is also immiscible in the other liquids including, but not limited to, whole blood, blood cell lysis reagent 22, and a wash liquid (as described below) such that it remains a distinct liquid phase throughout the pretreatment process.

Blood cell lysis reagent 22 is an aqueous liquid that includes one or more substances selected to lyse blood cells. In some embodiments, the composition of blood cell lysis reagent is selected such that blood cells are lysed without substantially affecting the integrity of microbial cells. Examples of suitable compositions of blood cell lysis reagent 22 are provided below.

FIG. 1(*b*) illustrates the addition of a volume of blood sample 26 to pretreatment vessel 20, where mixing of blood lysis reagent 22 with the blood sample 26 forms mixture 30 shown in FIG. 1(*c*). After providing a sample to pretreatment vessel (e.g. through pierceable rubber stopper 25), pretreatment vessel 20 may be agitated to produce further mixing of the sample with blood cell lysis reagent 22, as shown in FIG. 1(*c*). For example, pretreatment vessel 20 may be manually inverted one or more times to provide gentle mixing. In an alternative example, pretreatment vessel 20 may be vortexed at a low speed. A non-limiting example of a suitable low vortexing speed is a speed near approximately 300 rpm for a 4.9 mm orbit vortex mixer.

As stated above, the presence of blood cell lysis reagent 22 in mixture 30 causes the selective lysis of blood cells. In one example implementation, blood cell lysis reagent 22 may be an aqueous liquid including at least the following components: saponin, sodium polyanetholesulfonate (a sodium salt of polyanetholesulfonic acid, known as SPS), and an antifoaming agent, such as poly(propylene glycol) (PPG, e.g. with a molecular weight of approximately 2000). In some embodiments, the saponin is purified saponin. Example methods for purifying saponin are disclosed in U.S. Pat. No. 3,883,425, titled "Detoxification of Saponins", which is incorporated herein in its entirety. It has been found that without saponin purification blood cell lysis is less efficient and a gel-like substance is formed upon centrifugation.

In one example implementation, a composition of the blood cell lysis reagent, per approximately 1 mL of whole blood, may be provided as follows: an aqueous solution having a volume of approximately 500*μ*, and including approximately 75 mg/mL saponin (84510, Sigma), approximately 15 mg/mL sodium polyanetholesulfonate (SPS) (P2008, Sigma) and approximately 1% poly(propylene glycol) (PPG) MW 2000 (202339, Sigma). In one example implementation, the concentrations of saponin and SPS for 1 mL of whole blood may be in the range of approximately 4.5 to 240 mg/mL and 1.5 to 60 mg/mL, respectively. In another example implementation, the concentrations of the saponin and SPS for 1 mL of whole blood may be in the range of from approximately 30 to 90 mg/mL and 7.5 to 30 mg/mL, respectively. In other embodiments, lower concentrations of saponin may be employed, although blood cell lysis may not complete and more washing cycles may be required to remove blood cell debris. Also, higher concentrations of saponin may be employed, although the cell membrane of some microorganisms may be compromised, such that intracellular contents could be partially leaked.

SPS is an anti-coagulant and anti-phagocytosis agent. The mechanism by which SPS assists in blood cell lysis is not well understood. Without intended to be limited by theory, it is believed that the properties of SPS may reduce the incidence of entrapment of bacterial in cell debris and/or reduction of coagulated components which would sediment. SPS is, however, a known PCR inhibitor. At higher concentrations of SPS, more washing cycles may be employed to remove excess SPS, for applications in which a low concentration of SPS in the final extracted sample is desirable. The addition of PPG, an antifoaming agent, assists in maintaining a suitable viscosity of the mixture. It has been found that without the inclusion of PPG, the mixture may be thick and/or sticky.

After forming mixture 30 and agitating pretreatment vessel 20, pretreatment vessel 20 is centrifuged, as illustrated in FIG. 1(*d*). Pretreatment vessel 20 is centrifuged at a suitable rate and for a suitable time to cause microbial cells in mixture 30 to pass out of the suspension and collect at interface 32 between cushioning liquid 21 and supernatant 33 as shown in FIG. 1(*d*).

As noted above, cushioning liquid 21 has a density greater than that of mixture 30 and is immiscible with mixture 30 such that interface 32 is formed. This ensures that under centrifugal forces cushioning liquid 21 rapidly moves to the sedimentation region 34 and displaces supernatant 33, thereby forming a distinct fluid phase in the sedimentation region 34 of pretreatment vessel 20. Cushioning liquid 21 prevents the loss of microbial cells during the pretreatment process. Such a loss could otherwise occur due to adsorption and trapping of microbial cells on the surface of pretreatment vessel 20 within or near sedimentation region 34, but is substantially prevented in the present embodiment due to the presence of the liquid interface 32, where the microbial cells collect. Since the density of the cushioning liquid is greater than that of the cells the cushioning liquid prevents the cells from coming into close contact with the vessel walls or entering cavities in the wall which may otherwise trap said cells.

Figure 4A:
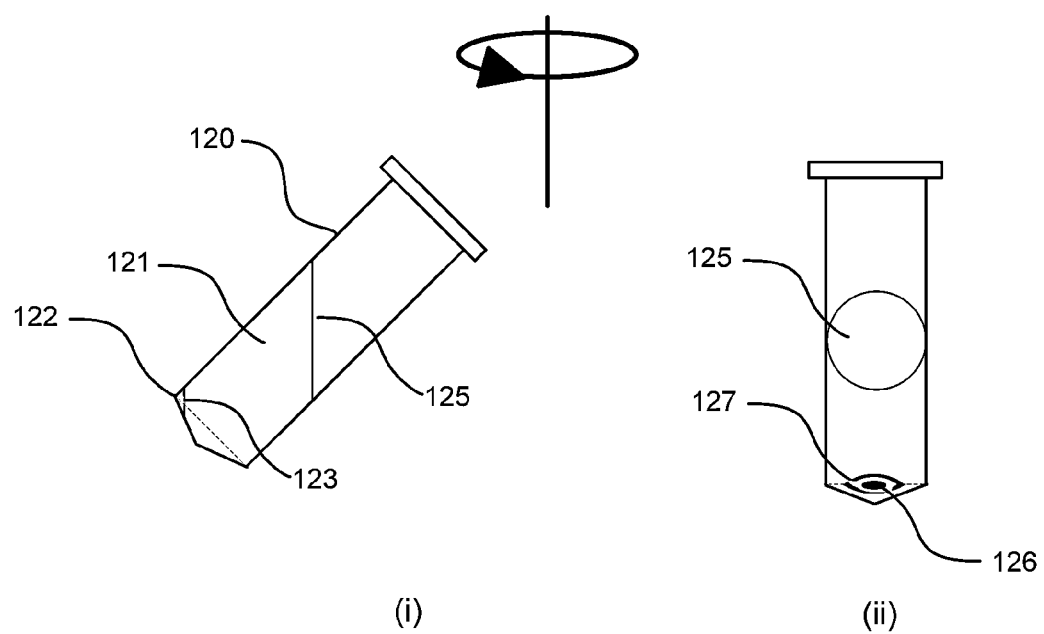
FIGS. 4(a)-(c) schematically illustrate three pretreatment vessels and their respective sedimentation zone in an angled centrifuge. In each case the tube is shown in radial section view (along the rotor radius) as (i) and in a view from the rotor axis in a direction perpendicular to the tube axis as (ii).
Figure 4B:
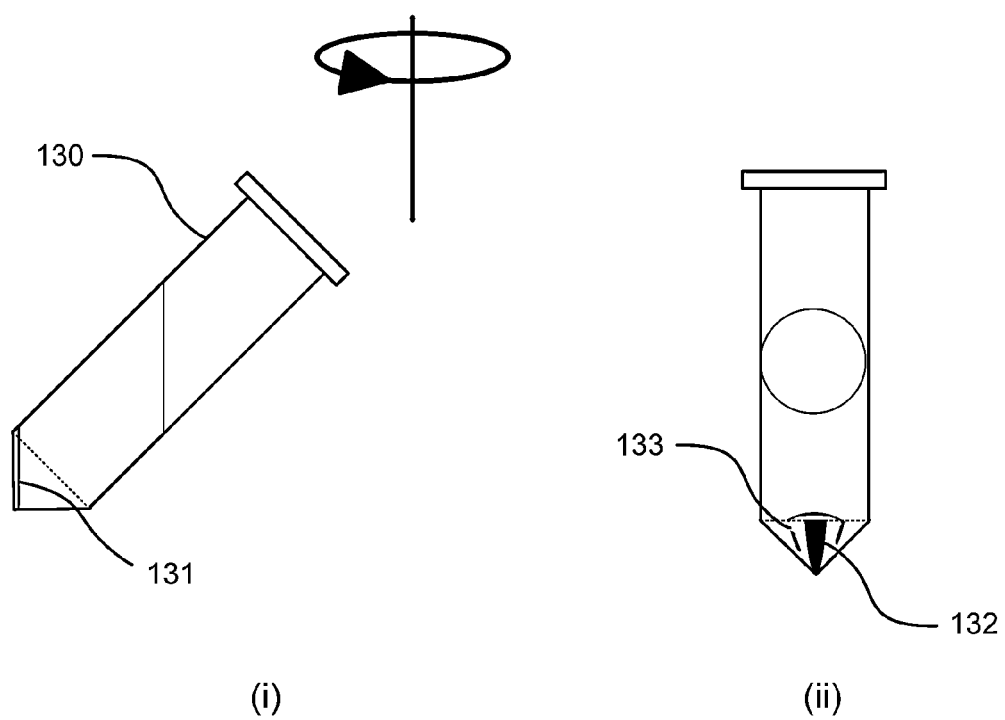
Figure 4C:
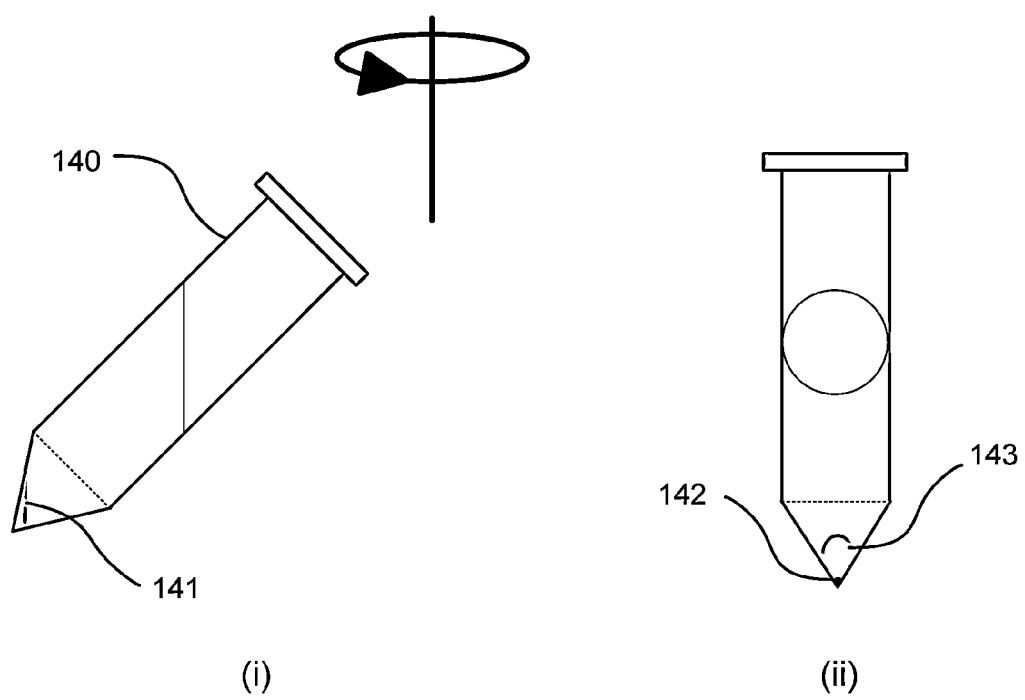

Fluorinated hydrocarbons, having molecular weight ranging from about 300 to 850, are suitable as cushioning liquids. Examples are FC-40, FC-43, FC-70, and FC-77. For the examples provided in this disclosure, Fluorinert™ FC-40 (F9755, Sigma) was used. The cushioning liquid volume should be sufficiently large to provide an adequately large sedimentation surface so that all target precipitate is collected on its surface. The minimum required cushioning liquid volume required to maximise target microbial cell recovery is dependent on a number of factors including the tube geometry, tube surface condition, centrifuge angle, centrifugal force and target cell sedimentation coefficient which are collectively termed centrifugal conditions. The guiding principle for determining the required minimum volume of the cushioning liquid volume is that the surface of the tube wetted by the cushioning liquid should at least envelop the region of the tube surface where the microbial cells would sediment in the absence of the sedimentation liquid. During centrifugation suspended cells move radially and when they encounter the tube wall they continue to move along the wall toward the extreme radial position until the component of the centrifugal force in the direction of the preferred movement is insufficient to overcome buoyancy and frictional forces which oppose cell motion. In the absence of the cushioning liquid the cells come to rest in a sedimentation region whose geometry reflects the centrifugal conditions. By providing cushioning liquid which envelops this region the cells will come into contact with the cushioning liquid either directly on its surface or on its periphery. By way of illustration FIGS. 4 (*a*), (*b*) and (*c*) show three different tube bottom angle geometries respectively in a 45 degree angle centrifuge. In each case the tube is shown in radial section view (along the rotor radius) as (i) and in a view from the rotor axis in a direction perpendicular to the tube axis as (ii). In FIG. 4(*a*) the tube 120 has a bottom cone angle which is approximately 25 degrees and contains a fluid 121 in which the target microbial cells are initially suspended. The surface of this fluid is shown in FIG. 4(*a*) (i) and (ii) as 125. In the absence of a cushioning liquid, after centrifugation for a sufficient duration at an appropriate speed the cells will come to rest at or near the radially outermost portion 122 of the tube which in this case is at the intersection between the cylindrical and conical portions of the tube. The sedimentation region 126 may extend a distance circumferentially on either side of the radially outermost point of the tube as shown in FIG. 4(*a*) (ii) due to the decreasing net force in the direction of movement of sedimenting cells which are moving along the wall toward the extreme radial position.

When a cushioning liquid is initially present in the tube and centrifugation is performed in its presence its surface 123 will approximately form a vertical plane and the cushioning liquid will wet the tube surface within the region 127 shown approximately in FIG. 4(*a*) (ii). In order to ensure that sedimenting cells come into contact with the cushioning liquid before coming to rest on the tube surface, the cushioning liquid should fully envelop the region 126 where sedimentation would have occurred in the absence of the cushioning liquid.

Likewise in a tube with a bottom cone angle of 45 degrees which matches the centrifuge angle in this example, shown in FIG. 4(*b*) as 130, the cushioning liquid will form a surface 131 as shown in FIG. 4(*b*) (i). The sedimentation zone 132 in the absence of the cushioning liquid will generally be distributed along the cone as shown in FIG. 4(*b*) (ii). The surface region 133 of the tube wetted by the cushioning liquid should at least envelop the sedimentation zone 132. When the tube bottom cone angle is greater than the centrifuge angle as shown in FIG. 4(*c*) the sedimentation zone is at the apex of the cone and the cushioning liquid 143 should envelop the sedimentation zone 142. It is evident from these examples that the minimum volume of cushioning liquid is dependent on the prevailing geometrical and sedimentation conditions. Swinging bucket or horizontally oriented centrifuges can likewise be considered and will generally have a sedimentation region at the apex of the tube which should be enveloped by the cushioning liquid. Other sedimentation vessels and centrifugal conditions can be similarly considered to determine the minimum cushioning liquid volume. Note that variability in the centrifugal conditions necessitates a cushioning liquid volume somewhat larger than the absolute minimum requirement determined as described above to ensure maximum recovery.

On the other hand the cushioning liquid surface should not be so large as to collect a substantial amount of blood cell debris and other unwanted material. Although the sedimentation rate of such material is generally much smaller than that of the target microbial cells, the high concentration of such material in the supernatant may result in sediment from fluid in the immediate vicinity of the cushioning liquid surface. Furthermore, a reduction in the amount of cushioning liquid will reduce the surface area of contact between the supernatant and the cushioning liquid and will prevent adsorption of unwanted material from the supernatant at or in its immediate vicinity. Another consideration in the selection of a maximum amount of cushioning liquid is supernatant extraction which occurs at rest during the wash steps described in this disclosure. Generally some of the collected cells will settle on the periphery of the cushioning liquid and some of these may remain on the tube wall even if the tube is reoriented. Since due to the presence of the cushioning liquid these are easily resuspended care and should be taken not to disturb this region with convective disturbances such as may occur due to aspiration of the supernatant so as to prevent loss of cells. Hence, in some embodiments, this periphery collection region should be distant from the aspiration device and optimally remain submerged in the residual liquid during aspiration of supernatant. A maximum volume of cushioning liquid is thereby related to the residual fluid volume and aspiration method. An example volume of cushioning liquid 21 is approximately 10 μL for a 2 mL pretreatment tube in an angle centrifuge operating at 10000 g. In another example embodiment, the volume of cushioning liquid may range between approximately 5 μl and 15 μl. In another example embodiment, the volume of sedimentation liquid may range between approximately 2.5 μl and 100 μl.

It will be understood that the centrifugation time and speed required to effect sedimentation of the microbial cells depends on the centrifuge radius, sample viscosity and density, and sedimentation path length and may be determined readily by those skilled in the art. For example, in one example embodiment, in which a blood volume of approximately 1 ml is injected into a 2 ml pretreatment vessel (with a suitable quantity of blood lysis reagents 22 and cushioning liquid 21 disclosed above) and placed in a fixed angle centrifuge, a centrifugal force of approximately 10000 g and a centrifugation time of approximately 1 minute is sufficient to sediment microbial cells of interest. It will be understood that other combinations of time, speed, and sample volume may be selected to achieve complete collection of the microbial cells at the cushioning surface 32.

After centrifugation, pretreatment vessel 20 may be reoriented in a position suitable for subsequent aspiration and dispensing operations, such as, for example, a vertical orientation as shown in FIG. 1(*e*), such that cushioning liquid 21 moves to the bottom of pretreatment vessel 20 and remains there due to gravity. This step may be performed sufficiently slowly such that convective disturbances in the liquid are minimised such that most or all of the microbial cells are prevented from being resuspended. The sedimented microbial cells may be deposited on the surface of the vessel proximal to the location of the sedimentation region or some cells may move with the cushioning liquid as it relocates under gravity.

The prevention of resuspension of cells enables the removal of most of the supernatant, as shown in FIG. 1(*f*), such that only a small volume of residual supernatant is left behind containing the retained microbial cells. For example, a syringe may be employed to remove a substantial portion of the supernatant. In order to achieve concentration of the retained microbial cells and to remove substances that could interfere with downstream processes, it is beneficial to remove as much of the supernatant as possible while leaving behind a sufficient volume of supernatant such that removal of the microbial cells in the aspirant is substantially avoided. Such an embodiment is effective in reducing the transfer of the blood cell debris and lysis reagents to the subsequent washing stages, and to the final pretreated sample. It is to be understood that in some embodiments, step (e) and step (f) may be performed with different orientations and positions of the pretreatment vessel and aspiration device. For example, in step (e) the pretreatment vessel may remain in the orientation of step (d) but be gently rotated 180 degrees in its holder such that the sedimentation region is now located at the bottom of the angled tube. This will allow aspiration of a greater amount of supernatant while leaving the sedimentation region undisturbed.

In one embodiment, the amount of the supernatant that is removed is between 80% and 95% of the total amount of supernatant. In an example implementation employing the quantities according to those described in the above example, a suitable aspirant volume is approximately 1.3 mL.

As shown in FIG. 1(g)-(k), one or more washing cycles may be optionally performed to purify the supernatant and to reduce the concentration of blood cell debris and blood cell lysis reagent present in the pretreated sample. Referring to FIG. 1(g), a volume of the washing liquid 35 may be added to sample pretreatment vessel 20. After addition of washing liquid 35, the solution is mixed to resuspend debris that may have sedimented or adsorbed to the vessel wall during centrifugation. This may be accomplished by vortexing as shown in FIG. 1(h). Pretreatment vessel 20 is subsequently centrifuged and re-oriented, and a substantial portion of the supernatant is removed, as shown in FIGS. 1(i) to (k), similar to the manner described for FIGS. 1(d) to (f).

In one example implementation, washing liquid 35 may be any low ionic strength aqueous medium such as salt solutions or buffers. The choice of lower ionic strength enables using the microbial cell lysate, following electrical or mechanical cell lysis, for molecular assays without requiring an ion balance step.

As noted below, the microbial cells are suspended in residual washing liquid 37 when the pretreated sample is extracted from pretreatment vessel 20. Accordingly it may be beneficial for the washing liquid 35 to have a composition suitable for downstream processing of the sample. In one example implementation, washing liquid 35 may include one or more reagents or media for preserving the viability of the retained microbial cells. For example, washing liquid 35 may include monovalent salt solution such as potassium chloride or sodium chloride. In another example, the washing liquid is a buffer such as phosphate buffer pH 7.4, Tris buffer pH 8.0. In another example, the washing liquid is a buffer that is compatible with downstream nucleic acid amplification reactions. In embodiments in which electrical lysis is performed subsequent to extraction of the pretreated sample (as described below), the ionic strength of the washing liquid should be selected such that it is compatible with working parameters of the electrical lysis method. For example, for the case of lysing microbial cells via electrical method, the ionic strength of washing liquid 35 may be between approximately 0.1 and 1 mM.

The number of wash cycles employed may depend on various factors, such as the desired level of dilution of the residual supernatant 36. For example, it may be useful to dilute supernatant 36 such that the residual concentration of SPS is less than approximately 0.01 μg/mL. In one example implementation, the wash sequence is not performed prior to extraction of the processed sample. In another embodiment, one wash cycle may be employed. In other embodiments, two or more wash cycles may be employed. In one example, based on the example parameters disclosed above, four wash cycles were found to provide effective removal of contaminants and inhibitory substances from the sample for downstream processing.

After performing the (optional) washing cycles, pretreatment vessel 20 may be agitated as is shown in FIG. 1(l), such that the retained microbial cells are resuspended in the residual supernatant 37. For example, pretreatment vessel 20 may be vortexed for approximately 5 to 20 seconds at a low speed, as described above.

After agitation, cushioning liquid 21 is allowed to settle at the bottom of pretreatment vessel 20, as shown in FIG. 1(m), such that pretreatment vessel 20 includes a residual suspension of the retained microbial cells above the cushioning liquid 21. This residual suspension may then be removed to obtain the extracted sample, referred to as the pretreated sample 38. In one embodiment, a substantial volume of the residual suspension is removed, such that little or none of cushioning liquid 21 is removed. Such an embodiment is beneficial in removing most of the retained microbial cells, while avoiding contamination by cushioning liquid 21. For example, the controlled removal of a selected volume of the residual suspension may be achieved via the insertion of a syringe with calibrated length, which may be inserted through pierceable rubber stopper 25, leaving cushioning liquid 21 behind.

In another embodiment, all of the residual suspension is removed, which may further include a small fraction of cushioning liquid 21. In yet another embodiment, in which one or more optional wash cycles are performed, both the residual suspension and a substantial portion of cushioning liquid 21 may be removed.

Although the preceding example embodiments relate to processing of whole blood as a sample matrix, it is to be understood that the methods disclosed herein may be adapted to the pretreatment of a wide variety of specimens. Suitable specimens include, but are not limited to, urine, sputum, cerebral spinal fluid, swabbed tissue samples, and other sample types of biological origin, and non-biological samples that may contain microbial samples. The initial sample may be combined with a reagent, buffer, or other medium prior to introduction into the pretreatment vessel.

FIGS. 2(a)-(c) and 3(a)-(b) illustrate two additional example embodiments for the pretreatment of a biological sample. Both FIGS. 2(a)-(c) and FIGS. 3(a)-(b) show the initial steps of alternative sample pretreatment embodiments, where the remaining steps are preformed according to the remaining steps (by Figure sub-letter) shown in FIG. 1.

In FIGS. 2(a)-(c), an embodiment is shown in which sample pretreatment vessel 20 includes a pretreatment buffer, reagent or liquid 100 that may or may not include a blood cell lysis reagent. For example, liquid 100 may be useful in stabilizing a sample other than a whole blood sample, such as sputum. Sample is added in step (b) and pretreatment vessel 20 is agitated in step (c), with the remainder of the steps performed as described above in relation to FIG. 1(a)-(m).

Figure 3:
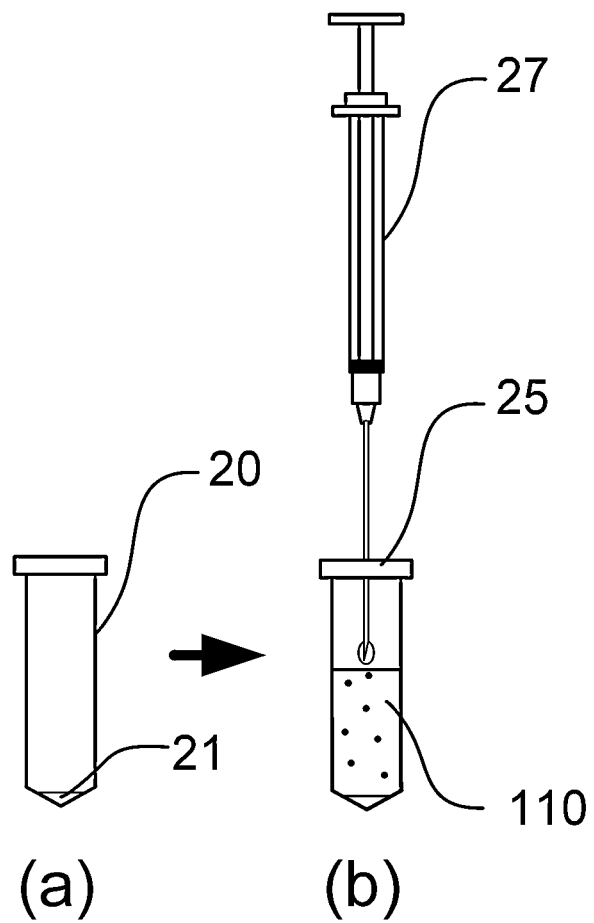
FIGS. 3(a) and (b) illustrate another alternative embodiment for performing pretreatment on a sample other than whole blood.

Similarly, FIGS. 3(a)-(b) show an example embodiment in which sample pretreatment vessel 20 initially includes cushioning liquid 21, to which sample, or a sample combined with a buffer, reagent or other liquid, is added in step (b). The remainder of the steps are performed as described above in relation to FIG. 1(a)-(m). Such an embodiment may be useful for the pretreatment of a urine sample, for example. Alternatively, the pretreatment of a urine sample may be performed according to a method similar to that disclosed in FIGS. 2(a)-(c), where liquid 100 includes a blood cell lysis reagent for the lysis of blood cells that may be present in the urine sample.

In some embodiments, the sample pretreatment processes disclosed above, or variations thereof, may be automated to reduce the operator involvement and to improve cell collection and washing effectiveness. For example, a centrifuge that is configured with the ability to perform automated wash steps may be employed for this purpose.

Figure 5A:
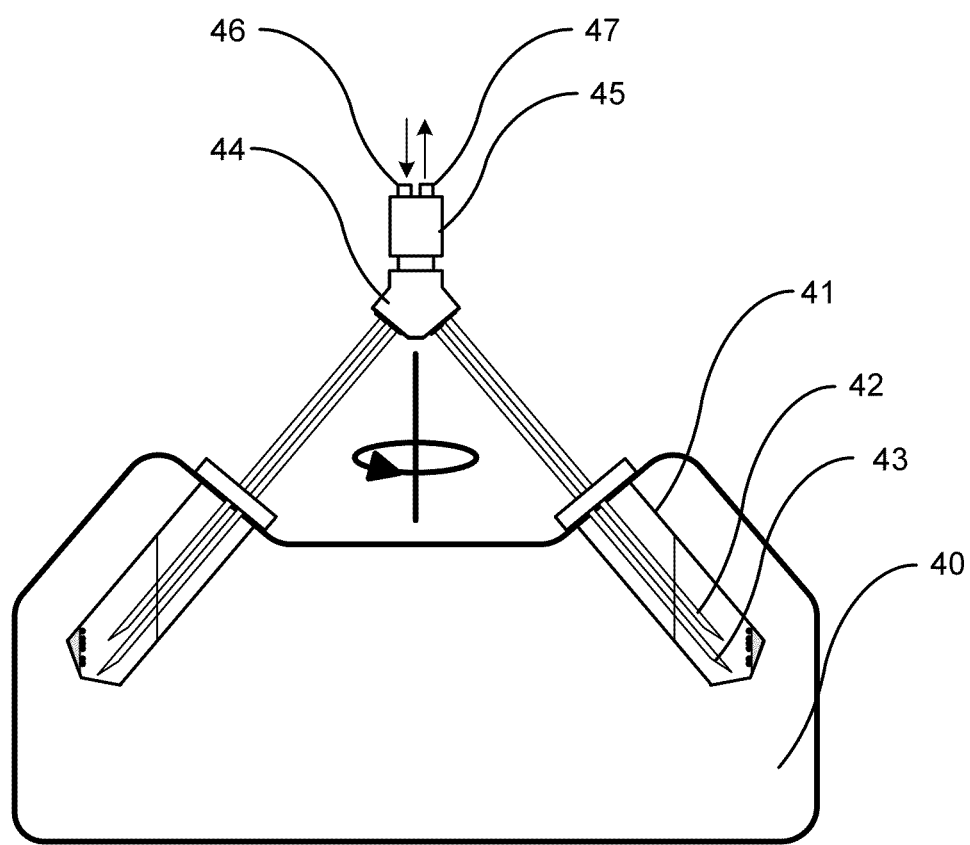
Figure 5B:
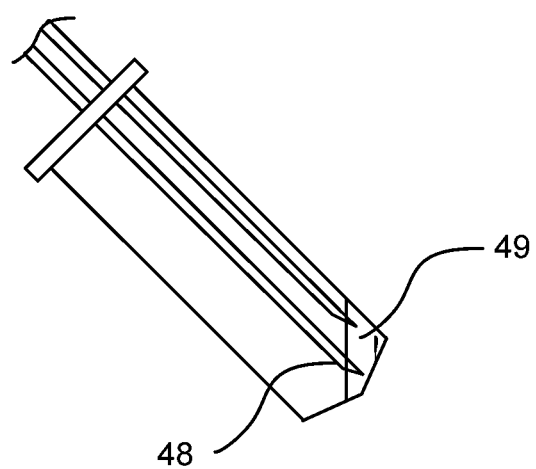
Figure 5C:
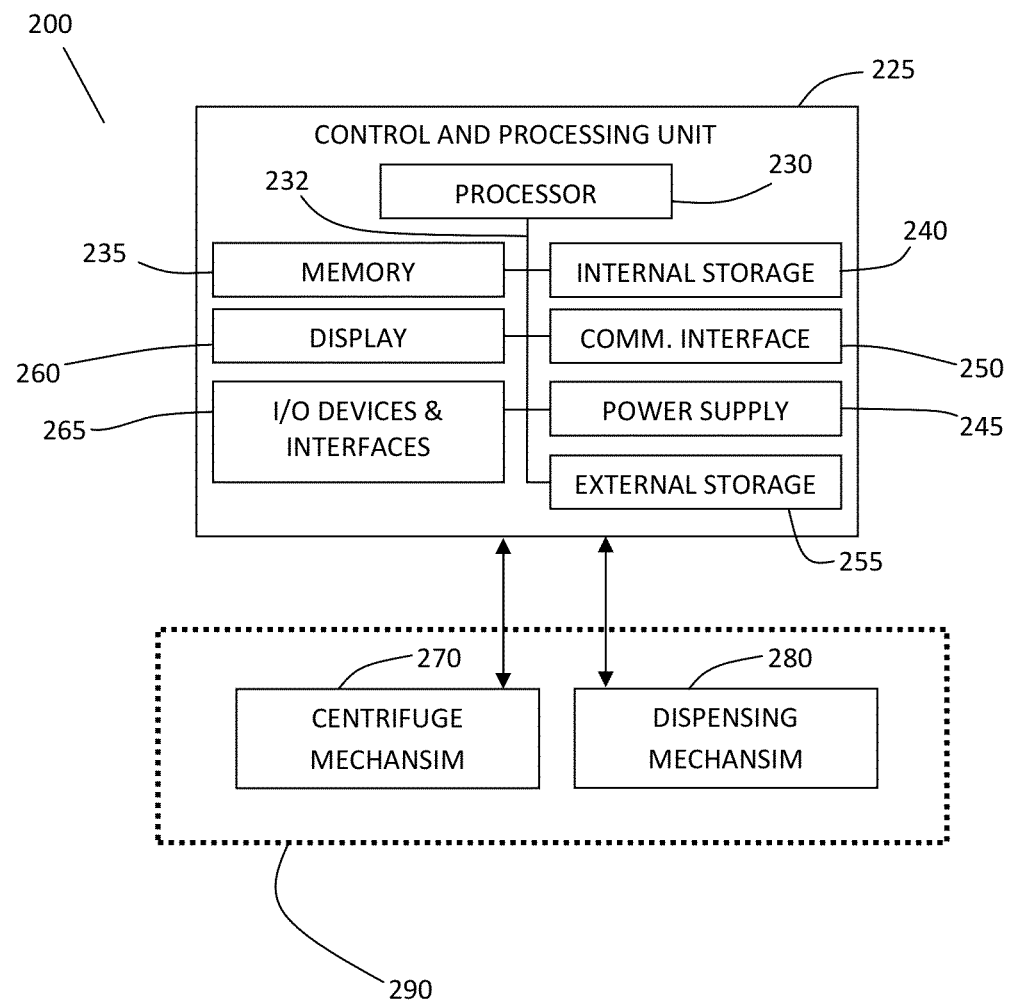
FIG. 5(c) illustrates an example control and processing system.

FIGS. 5(a)-(c) illustrates an example implementation of an automated device for use in sample pretreatment, including a centrifugation mechanism that is integrated with a washing mechanism. FIG. 5(a) shows a diametrical cross-sectional view of a centrifuge with a closed aspirant path. The centrifuge is powered by a motor capable of achieving speeds and centrifugal forces described in the aforementioned embodiments.

Rotor 40 contains receptacles for a plurality of pretreatment tubes 41. A dispensing tube 42 and an aspirant tube 43 are inserted into the pretreatment tube 41 by piercing the pierceable top cap of the pretreatment tube. Dispensing tube 42 and aspirant tube 43 may be provided according to a number of different configurations, such as concentrically, or in a parallel/adjacent configuration as shown in FIGS. 5(a) and (b). The dispensing and aspiration tubes, or the plurality of dispensing tubes and aspiration tubes in the case of multiple pretreatment tubes for simultaneous pretreatment, terminate at a manifold 44 which is fluidically connected to a rotating union 45. The rotating union 45 is provided to allow fluidic connection during rotor rotation of the dispensing and aspiration paths to entrance and exit tubes 46 and 47 respectively which are stationary. Such rotating unions are available commercially and may be designed for rotational speeds disclosed herein.

Entrance tube 46 and exit tube 47 may be connected to a dispensing fluid source and waste reservoir respectively, each of which are provided with a dispensing mechanism (such as a peristaltic pump or a syringe pump) for independently dispensing and aspirating fluids. The vortexing, dispensing, and aspiration actions may be controlled independently by the device in accordance with a pre-programmed treatment protocol, following one or more of the steps outlined in FIG. 1(a)-(m), in an automated fashion, instead of a manual fashion. Vortexing may be accomplished, for example, by varying rotational speed, rotational stop/start cycles, rapid alternating rotational direction cycles, and other suitable motions of rotor 40. Alternatively a vibratory mechanism may be applied to the rotor at rest or located on the rotor to apply the forces necessary to resuspend sediment and mix the fluids as required by the pretreatment process described. Following sedimentation steps, aspiration may be performed while rotor 40 rotates at a speed for which the sedimentation liquid and cells are held in the sedimentation region with the aspiration tube so positioned as to prevent disturbance of the sedimented microbial cells and avoid aspiration of the sedimentation liquid or the microbial cells. With proper placement of the aspiration tube a small residual may be achieved which in turn may increase the wash efficiency. For example FIG. 5(b) illustrates an aspiration tube placement 48 and residual fluid volume 49 which may be achieved without disturbing the sedimented cells and the cushioning fluid when aspiration occurs during rotor rotation.

The pretreatment protocol may be performed with the automated centrifuge washer in the following manner. With reference to FIG. 1, the sample insertion steps (b) may be performed manually and the pretreatment tubes so prepared are placed in the centrifuge washer. The dispensing and aspiration tubes are inserted into the pretreatment tubes as described above and the manifold connections made. The centrifuge washer is pre-programmed and operated in accordance with the desired parameters for the subsequent series of vortexing, centrifugation, aspiration and dispensing steps analogous to the steps of FIG. 1 (c) to (l) in order to perform the required sample treatment and washing actions. It is to be understood that some or all of the steps shown in FIGS. 1(c)-(l) may be automated without re-orienting the pretreatment tube. The pretreatment tubes are then removed from the centrifuge washer and the aspiration step of FIG. 1(m) is performed manually.

As shown in FIG. 5(c), centrifuge mechanism 270, and liquid dispensing mechanism 280, may be connected to, or connectable to, a control and processing unit 225 for controlling the operation of the liquid dispensing and centrifuge mechanisms according to the presently disclosed sample pretreatment methods. Control and processing unit 225 may include one or more processors 230 (for example, a CPU/microprocessor), bus 232, memory 235, which may include random access memory (RAM) and/or read only memory (ROM), one or more internal storage devices 240 (e.g. a hard disk drive, compact disk drive or internal flash memory), a power supply 245, one more communications interfaces 250, external storage 255, a display 260 and various input/output devices and/or interfaces 255.

Although only one of each component is illustrated in FIG. 5(c), any number of each component can be included in the control and processing unit 225. For example, a computer typically contains a number of different data storage media. Furthermore, although bus 232 is depicted as a single connection between all of the components, it will be appreciated that the bus 232 may represent one or more circuits, devices or communication channels which link two or more of the components. For example, in personal computers, bus 232 often includes or is a motherboard.

In one embodiment, control and processing unit 225 may be, or include, a general purpose computer or any other hardware equivalents. Control and processing unit 225 may also be implemented as one or more physical devices that are coupled to processor 230 through one of more communications channels or interfaces. For example, control and processing unit 225 can be implemented using application specific integrated circuits (ASICs). Alternatively, control and processing unit 225 can be implemented as a combination of hardware and software, where the software is loaded into the processor from the memory or over a network connection.

Control and processing unit 225 may be programmed with a set of instructions which when executed in the processor causes the system to perform one or more methods described in the disclosure. Control and processing unit 225 may include many more or less components than those shown.

Figure 6A:
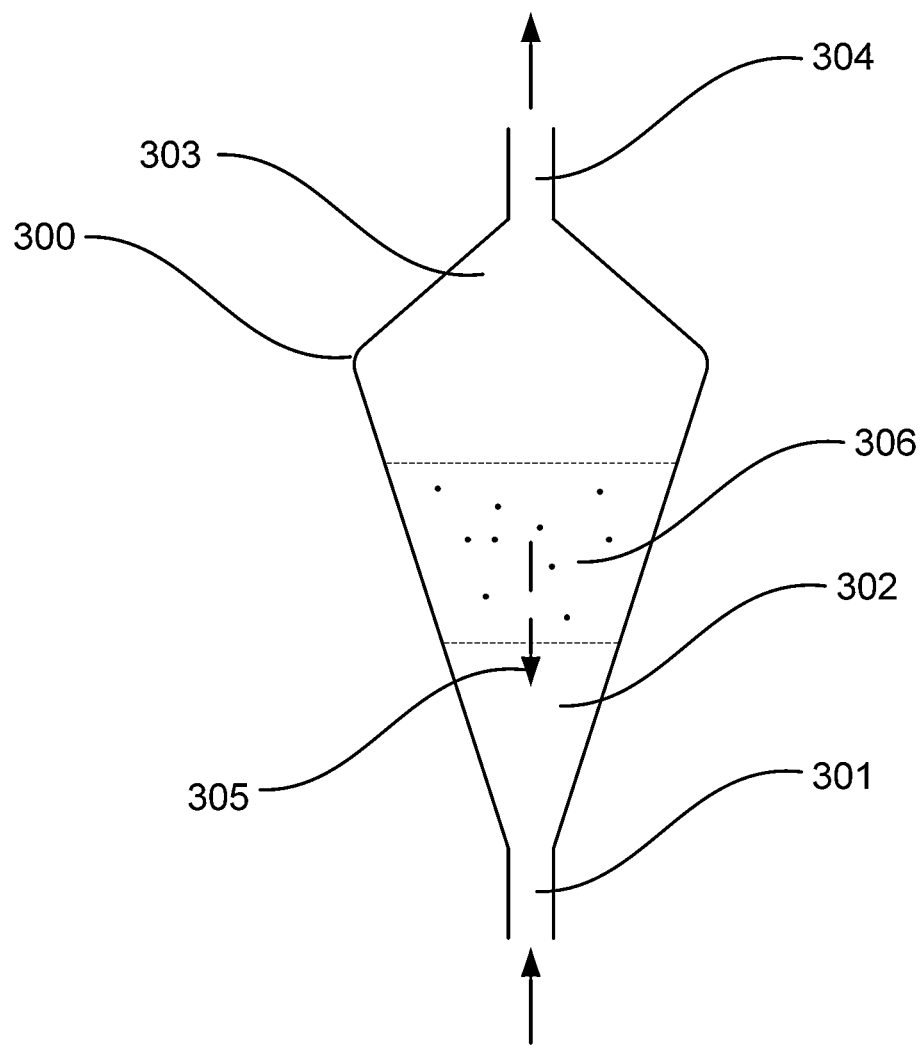
FIGS. 6(a)-6(c), 6(d)(i), 6(d)(ii) and 6(e) illustrate alternative embodiments for automation of the sample pretreatment method.

FIGS. 6(a)-(e) illustrate alternative devices which allow automation of some steps of the pretreatment process. FIG. 6(a) portrays an elutriation device 300 which is operated in accordance with the principles of counterflow centrifugal elutriation. The elutriation device consists of an inlet tube 301, a conical collection chamber 302 opening in the direction of fluid flow, and an exit cone 303 and outlet tube 304. The elutriation device is placed in a centrifuge rotor and rotated such that the centrifugal force 305 or a sufficient component thereof is directed along the axis of the elutriation device. The fluid suspension is passed through the device flowing from the inlet tube 301, through the collection chamber 302, and exiting through the outlet tube 304. While passing through the collection chamber the particles are subjected to centrifugal forces which oppose the flow direction such that particles with sedimentation coefficients less than a predetermined magnitude are prevented from flowing out of the collection chamber as the fluid flows outward through the chamber outlet 304. The collection zone 306 within the collection chamber is dependent on the centrifugal force and flow velocity both of which vary with position and can be predetermined by choosing appropriate chamber dimensions and centrifuge operating speed.

In the context of the current disclosure the initial pretreatment steps of FIG. 1 (a) to (c) are completed in a separate pretreatment vessel and the pretreatment fluid/sample mixture is passed through the elutriation device as described above. The cells thereby remain suspended in the collection chamber while the full volume of the pretreatment fluid mixture is passed through the chamber. A further volume of wash buffer is passed through the chamber so as to displace the pretreatment fluid and produce a clean cell suspension thus eliminating any contaminants that may be detrimental to subsequent sample processing. In this embodiment the presence of the cushion liquid is not required as cells are held in suspension throughout the centrifugal process and therefore loss of cells due to entrapment or adsorption on the chamber surface will not occur. The final pretreated cell suspension is obtained by lowering the centrifuge speed and/or increasing the flow rate thereby allowing the cell suspension to exit through the outlet tube 304 to a pretreated sample collection device. Alternatively the cell suspension may be removed by reversing the flow and removing the fluid from the chamber via the inlet tube 301 either during or after stopping centrifugal rotation.

Since it is also generally necessary to concentrate the cells in a smaller fluid volume than the original sample the elutriation chamber should be of an appropriate size to allow extraction of the suspended cells into the desired pretreated sample volume. Thus an elutriation chamber volume may be similar in size to the final sample. For example the pretreatment fluid/sample volume used in examples herein is approximately 1.5 ml and a preferred final clean cell suspension volume is approximately 50 µl for some applications. For a typical elutriation chamber geometry with a volume of approximately 50 µl and typical benchtop centrifuge parameters the elutriation flow rate is limited to approximately 1 µl/second for which the total elutriation time amounts to processing times of approximately 30 minutes. This processing time can be substantially reduced by initially performing steps (a) to (f) followed by steps (l) and (m) of FIG. 1 to obtain a concentrated pretreatment fluid/sample volume and performing the wash steps in the current elutriation device with the reduced volume.

Figure 6B:
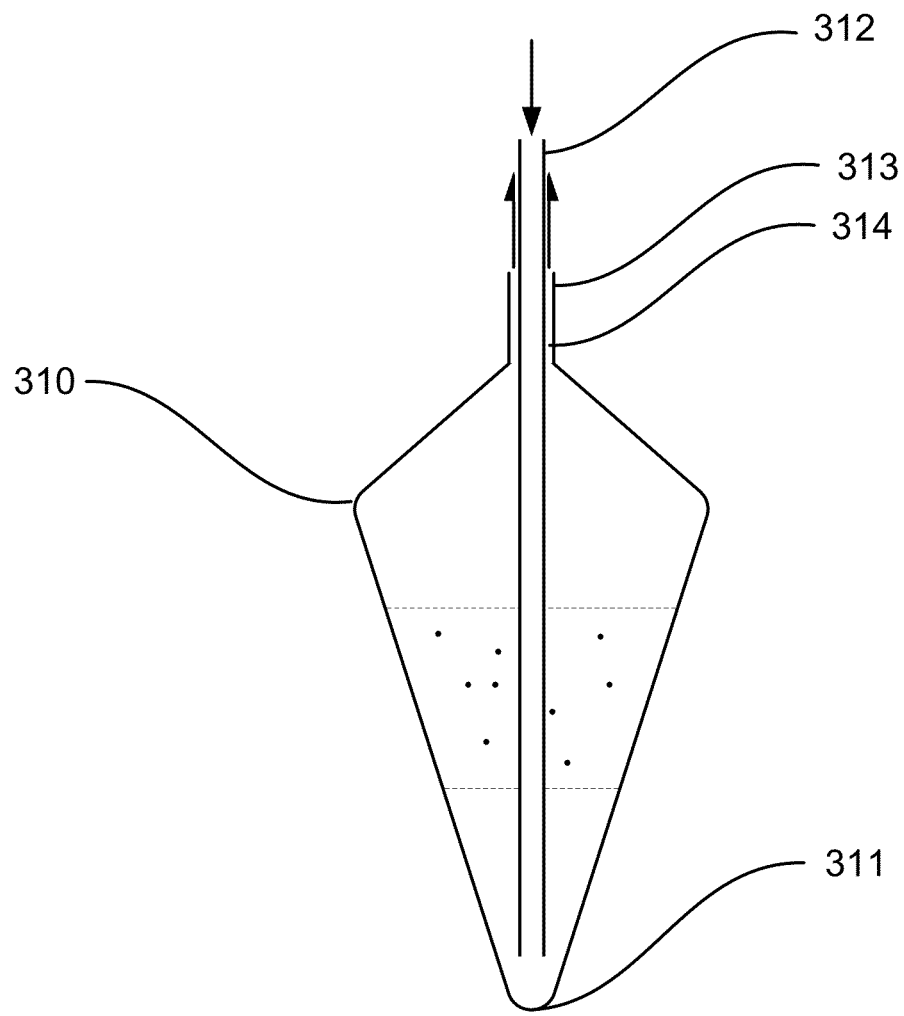
Figure 6C:
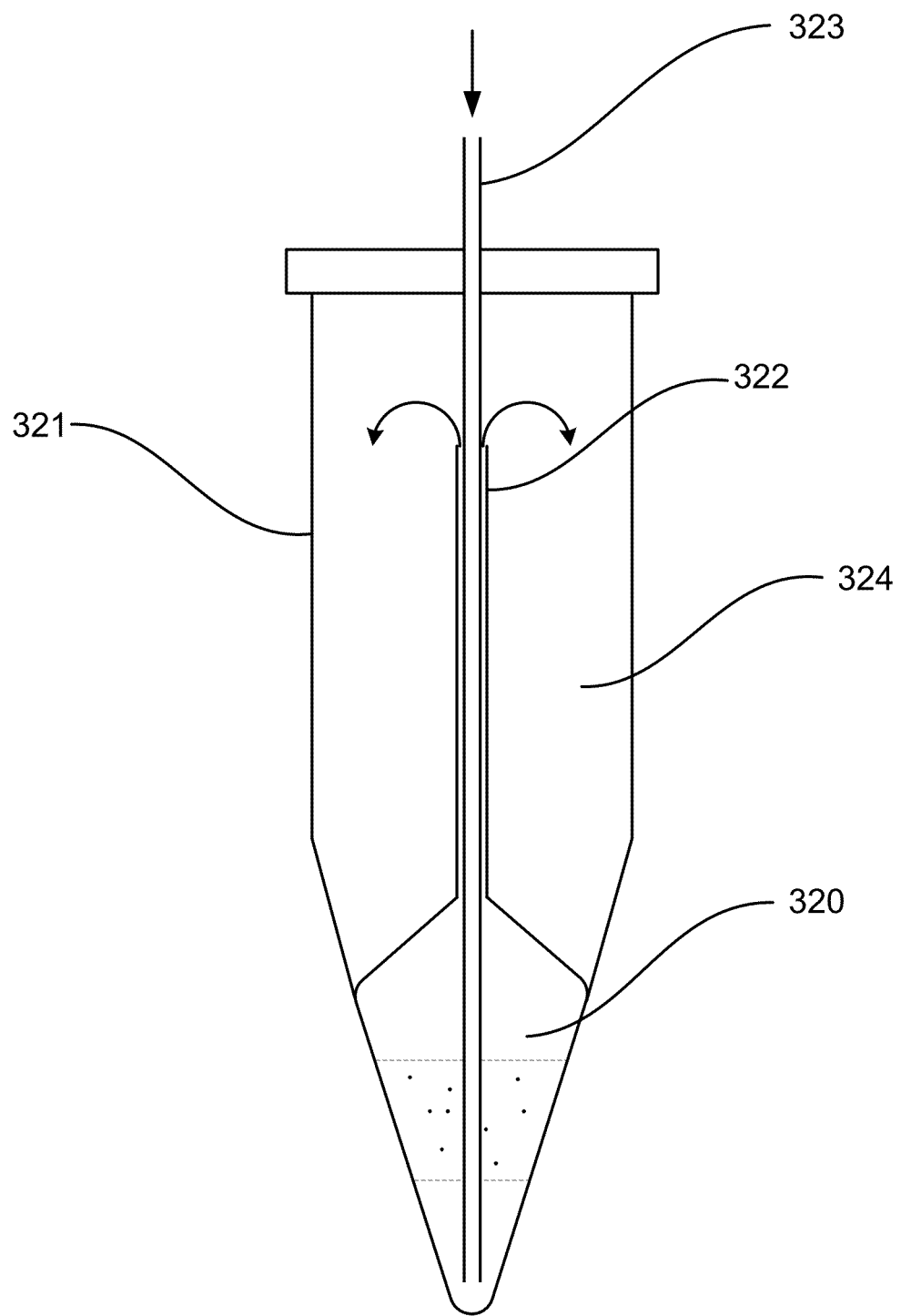

An alternative pretreatment device 310 is shown in FIG. 6(b) which is similar in function to the elutriation device of FIG. 6(a) but differs in some aspects. In this case the elutriation chamber has a closed bottom 311 and the inlet tube 312 is inserted through the outlet tube 313 such that the incoming fluid is dispensed close to but at a predetermined distance away from the bottom of the tube. The outgoing fluid flows from the annular outlet 314 created by the inlet and outlet tubes. The operation of this device is similar to that of the elutriation device described above but its design allows access to both the chamber inlet and outlet from one end of the device. A related embodiment is shown in FIG. 6c in which the elutriation chamber 320 is integral to a centrifuge tube 321 and the elutriation chamber outlet tube 322 exits into an isolated waste chamber 324. A similar embodiment can be envisaged for the flow-through embodiment of FIG. 6(a). The waste chamber prevents contamination of external waste flow paths and retains all fluid waste within the device which is advantageous for safe operation and disposal of potentially hazardous sample fluids. For this embodiment it is preferred to remove the cell suspension by drawing the fluid from the chamber through the inlet tube 323 in the reverse direction to the fluid flow during operation. The outlet tube 322 extends beyond the surface of the waste fluid under the conditions prevailing when washing is complete and the clean cell suspension is removed from the elutriation chamber.

Figure 6D:
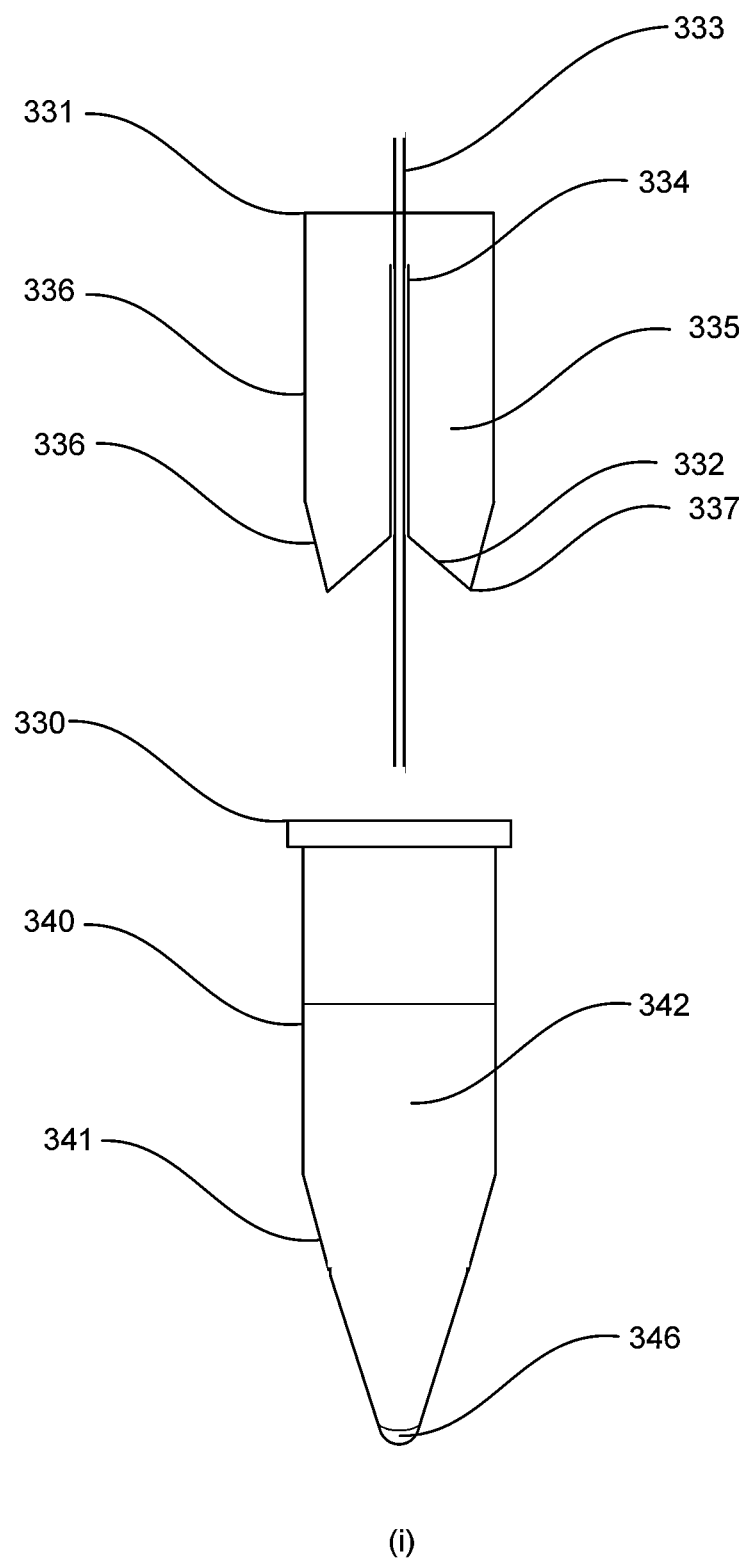
Figure 6D:
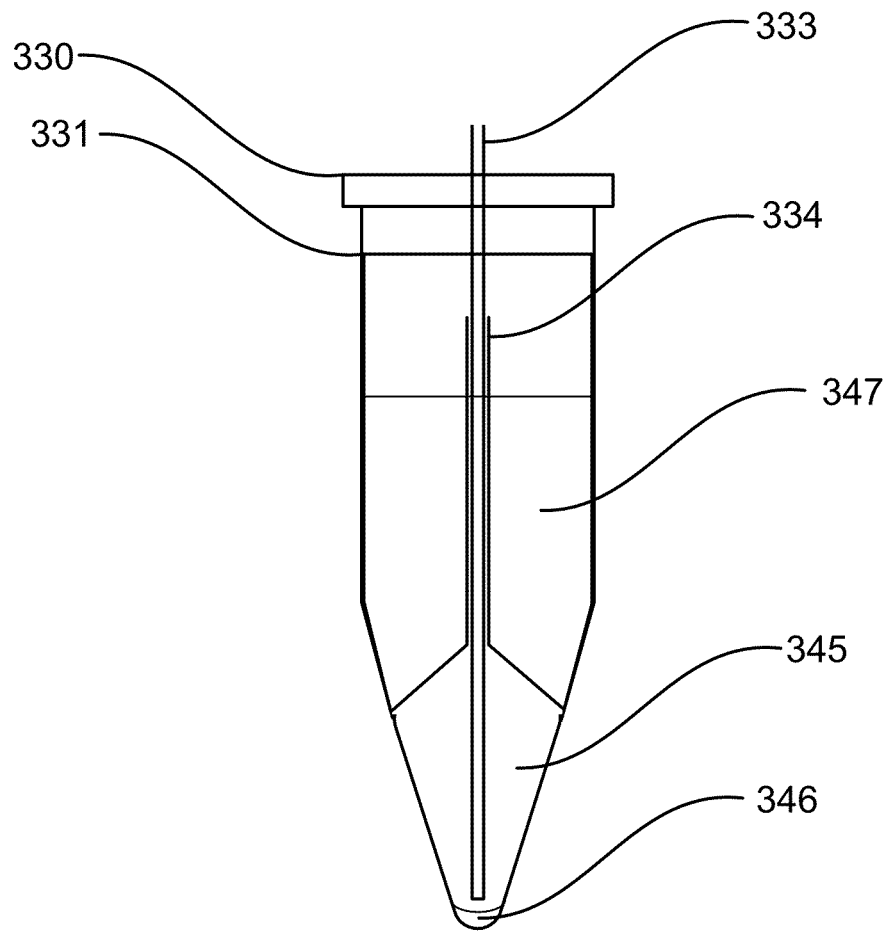

A further embodiment is shown in FIG. 6(d) which extends the concept of FIG. 6(c) to a two part device consisting of a first part 330 which is the centrifuge tube and the second part 331 which includes the elutriation exit cone 332, inlet tube 333, outlet tube 334 and waste chamber 335 as shown in FIG. 6(d) (i). The main body of the second part 331 has a cylindrical outer surface 336 and is insertable into the cylindrical portion 340 of the first part and may be pushed into said first part until the bottom portion 336 of the second part engages with the bottom portion 341 of first part as illustrated in FIG. 6(d) (ii). The extremity of the bottom portion of the second part is so formed that it seats tightly with the bottom portion of the first part such that a seal is obtained between the first and second parts thus forming an isolated chamber 345 with inlet tube 333 and outlet tube 334. A deformable portion or material such as a rubber gasket may be provided at the extremity 337 of the second part to provide an adequate seal.

Figure 6E:
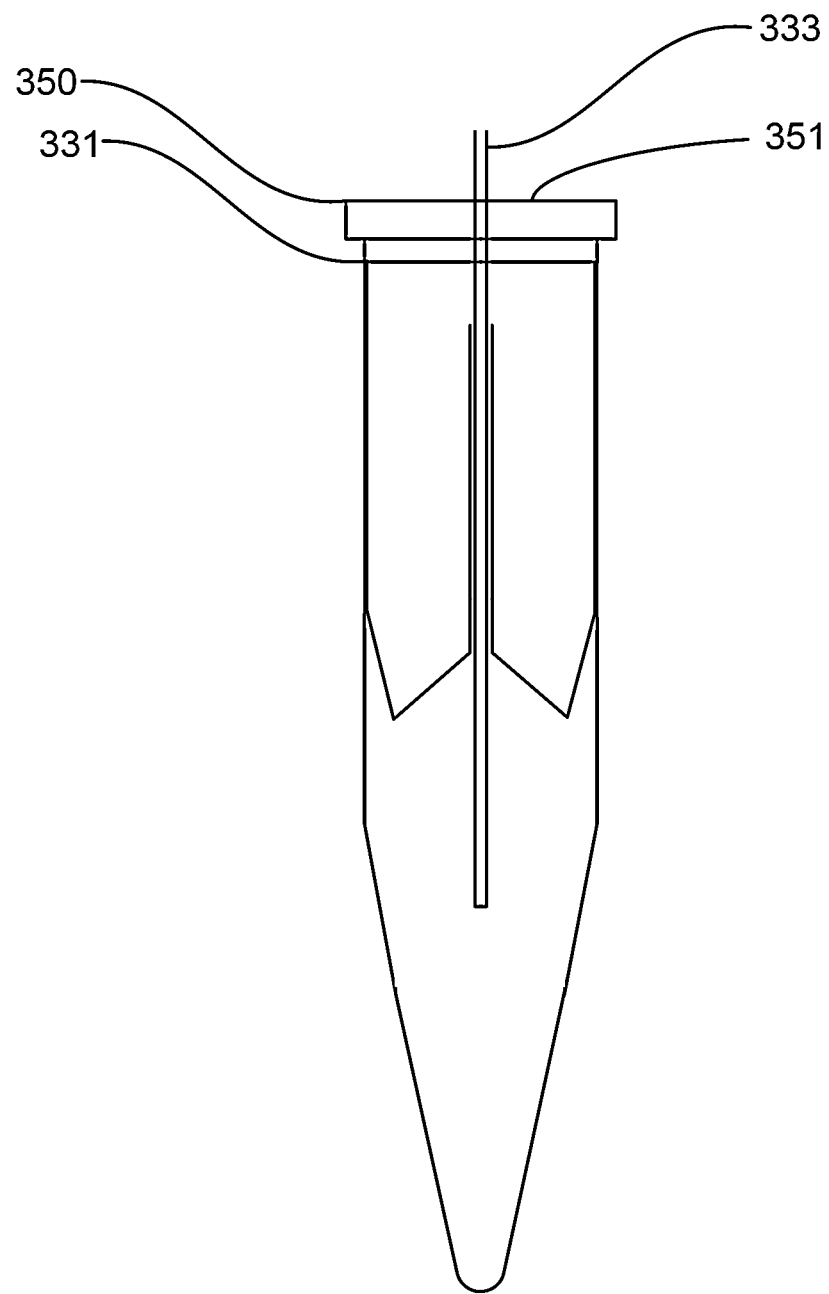

The pretreatment fluid/sample mixture 342 containing the cushioning fluid is initially dispensed into the first part of FIG. 6(d) and subjected to centrifugation such that the microbial cells sediment on the surface and periphery of the cushioning fluid 346 at the bottom apex of the tube. Optionally the first part 330 contains a volume of blood lysis reagent and cushioning liquid as described previously and the sample is inserted, followed by mixing so as to produce a mixture and effect lysis of the blood cells, and is subsequently subjected to centrifugation. Following sedimentation of the microbial cells the second part 331 is inserted into and pushed to the bottom of the first part 330 sufficiently slowly to allow the supernatant so displaced to flow through the outlet tube and into the waste chamber resulting in the engaged position of the parts as shown in FIG. 6(d) (ii). In this way a large portion of the supernatant 347 is separated from the chamber 345 and a washing step may proceed within the smaller chamber volume. Hence the washing function can proceed by rotating the engaged tube assembly while flowing wash fluid through the inlet tube into the chamber. Cells which were sedimented on the cushioning liquid at the bottom of the chamber may be disturbed by the incoming flow but will be retained in the chamber due to centrifugal forces which exceed flow induced forces on the cells due to the controlled flow rate. The wash fluid will displace pretreatment fluid and non-sedimenting particles to produce a clean fluid in the chamber. In order to improve the washing efficiency the fluid in the chamber may be mixed by vibration or vortexing intermittently in order to resuspend particulate that may attach to the chamber wall and to dilute fluid zones of relative stagnation. Furthermore the density of the wash fluid may be increased to a level exceeding that of the pretreatment fluid/sample mixture by, for example, the addition of trehalose to provide a more effective displacement of pretreatment fluid/sample mixture from the chamber. FIG. 6(e) illustrates an alternate embodiment for which the second part 331 is inserted into a first part 350 prior to operation of the device. Optionally the inlet tube 333 may be a separate device which is inserted through a pierceable membrane 351 at the top of the tube. The inlet tube 333 may optionally also be used to insert the sample or the pretreatment fluid/sample mixture into the tube.

In some embodiments, the preceding embodiments may be employed for the initial extraction and concentration of microbial cells, followed by downstream methods for identifying microbial cells using both the reverse transcription of rRNA into complementary DNA (cDNA), with subsequent amplification and detection of the cDNA. The amplification of cDNA may optionally be performed simultaneously, or serially, with the amplification of genomic DNA, where the cDNA and the gDNA are employed for identifying different genotypic taxa of the microbial cells. The gDNA may be obtained from the same lysate as the rRNA.

Microbial cells that may be identified according to embodiments of the disclosure include bacteria and fungi. In some embodiments, rRNA from the microbial cells is released, and a reverse transcription step is employed to obtain cDNA, where the cDNA is representative of a first genotypic taxa level, and where the cDNA, if present, is subsequently amplified and detected in order to identify the first genotypic taxa level of the microbial cells. Simultaneously or sequentially, amplification and detection of gDNA released from the microbial cells is employed to identify a second genotypic taxa of the microbial cells of a second level, where the second level is of a lower level than the first level.

Figure 7A:
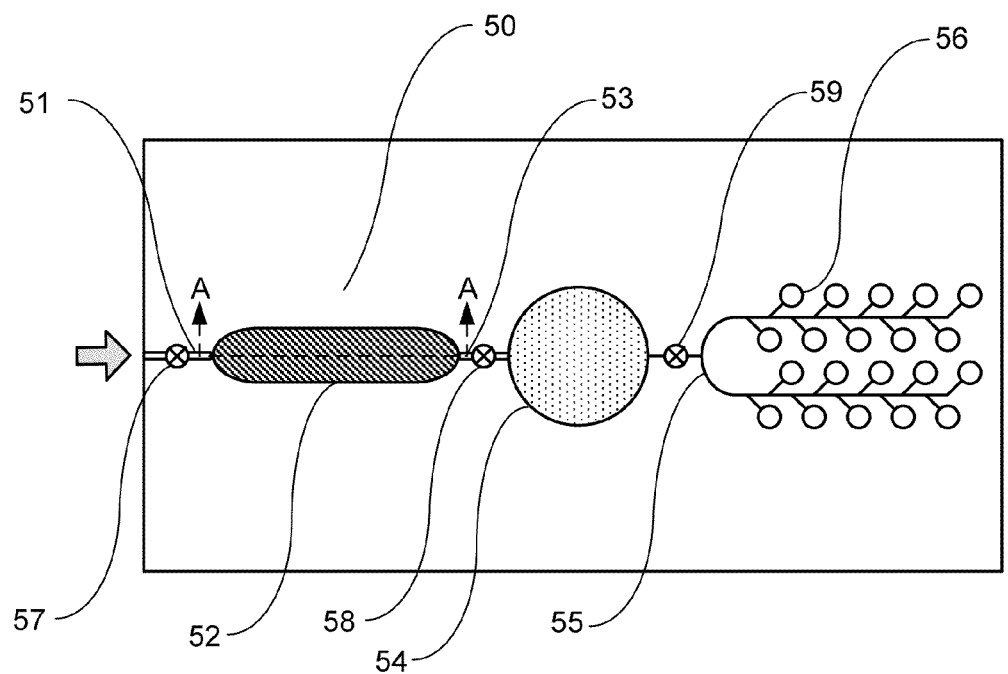
FIG. 7(a) schematically depicts an example fluidic device for performing electrical cell treatment, rRNA reverse transcription, PCR, and amplicon detection.

An example module for performing electrical treatment, reverse transcription of rRNA, PCR, and amplicon detection is schematically presented in FIG. 7a. Electrical channel 52 includes an inlet port 51 through which fluid sample and other fluids may be introduced. Electrical channel 52 also includes outlet port 53, which is in fluid communication with downstream thermal chamber 54, where the molecular amplification may be performed. Flow along electrical channel 52 is provided by a pressure differential between inlet 51 and outlet 53 ports.

The device may include additional fluid features, such as valves for opening and closing ports 51 and 53. For example, valves 57 and 58 may optionally be provided at the inlet 51 and outlet ports 53 of electrical channel 52, and valve 59 is optionally provided at the outlet of thermal channel. Valves 57, 58 and 59 may employ any suitable valving mechanism compatible with a microfluidic channel, including, but not limited to, pinch valves, ball valves, disc valves, plug valves. Valves 57 and 58 may be provided to assist in controlling evaporation of the liquid during electrical lysing and treatment and to control the exposure of the fluid to electrical field and thermal effects. For example, valves 57 and 58 may be useful in ensuring that a sufficiently high temperature is achieved for sufficient and/or efficient e-lysis (for example, some organisms, such as fungi, may require higher temperatures and/or temperature rates of change for efficient lysis).

Figure 7B:
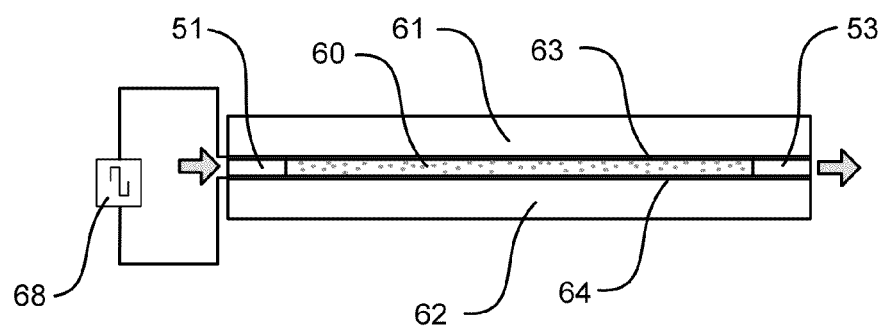
FIG. 7(b) schematically depicts the cross section A-A of electrical chamber 52 of FIG. 5 and shows the application of voltage pulses to the electrical chamber.

Referring now to FIG. 7b, cross section A-A of electrical chamber 52 of FIG. 7a is shown along with a circuit for applying voltage pulses to the electrical chamber. Electrical treatment of the processed sample may be performed, for example, according to methods disclosed in co-pending PCT Application Number PCT/CA2012/000698, titled "METHODS AND DEVICES FOR ELECTRICAL SAMPLE PREPARATION" and filed on Jul. 25, 2012, which is incorporated herein by reference in its entirety. The device includes a thin channel defined on one side by the top plate 61, electrode 63 and on the opposite side by base plate 62 and electrode 64. The upper and lower portions are separated by a thin spacer, in which material is removed to form the channel cavity. The spacer may be made from a dielectric material, which may be slightly deformable under an applied clamping pressure, or which is bonded to the upper and lower surfaces of the channel cavity. The spacer thus defines the side walls of the channel, provides the fluid seal, and electrically insulates the top and bottom electrodes from each other.

The lower electrode 64 and upper electrode 63 are electrically isolated from the base and top plates (substrates) by lower and upper electrically insulating layers. In accordance with thermal requirements, thermal insulating layers may also be provided which may be separate from or be suitable selections of the electrical insulating material. The channel has dimensions H×W×L which, in one example implementation, used for the tests in the following examples it was $0.2 \times 6.4 \times 15$ mm$^3$. The two electrodes 63 and 64 are intended for inducing an electric field across the channel resulting in the establishment of an ionic current.

As per the methods disclosed in PCT Application Number PCT/CA2012/000698, the application of suitable amplitude modulated electric pulse train by the external voltage source 68 on the two electrodes, establishes an electric field in the electric chamber. The electric field results in ionic current and Joule heating of the liquid. As the duration of the electric pulse train and, consequently, the accompanying Joule heating is brief, this mechanism of heating is known as flash heating. The coupled effect of the electric field acting on the cells and the flash heating of the liquid causes the microbial cells to lyse and intracellular molecules, such as proteins and nucleic acids, to be released from the cell as a lysate. The lysis process, which will be referred as E-Lysis in the context of the present disclosure, irreversibly permeabilizes the microbial cell membrane and readily supports molecular exchange in and out of the cell.

The macromolecular content of the cell may undergo a transformation in the period between turning on of the electric field and cooling down of the liquid. This process, identified herein as E-treatment, renders nucleic acids, such as rRNA and gDNA, more accessible to enzymes, thus improving the efficiencies of the ensuing nucleic acid amplification processes. Moreover, E-treatment inactivates most of enzymes that are released from microbial cells or have been left in the channel from residual blood cell debris. Thus, the deleterious inhibitory effects of such enzymes in the subsequent processes are minimized.

Referring again to FIG. 7a thermal chamber 54 is provided for performing reverse transcription of rRNA followed by the PCR. After the introduction of the treated sample into thermal chamber 54 along with the reverse transcription PCR master mix, the resulting mixture is incubated and thermally cycled as necessary. The master mix may be introduced in liquid form or may be present in the chamber in dry format prior to the introduction of the sample. In one example embodiment, the heating and cooling operations may be provided by placing the device on a Peltier device. In other embodiments, heating may be provided by electrical resistance contact heaters, radiant heating, or convection heaters and cooling may be provided by circulating fluids, forced air flow etc. The nucleic acid sequences of the rRNA are reverse-transcribed to complementary DNA (cDNA). The reagent for reverse transcription typically contains reverse transcription enzyme, deoxy nucleotide triphosphate mixture (dNTPs), an appropriate buffer with magnesium or manganese cofactor, and optionally RNase inhibitor. The reverse transcription can be any RNA-dependent DNA polymerase enzyme known in the prior art such as Moloney Murine Leukemia Virus (M-MuLV) reverse transcription, Avian Myeloblastosis Virus (AMV) reverse transcription and *Thermus thermophilus* (Tth) DNA polymerases.

The primers can be non-specific random primers or gene-specific primers. In some embodiments, nucleic acid sequences of no more than 500 bases will be reverse transcribed to cDNA using gene-specific primers. The specific primers can be primer sets or degenerate primers. One or more target nucleic acid sequences of one or more microorganisms will be reverse transcribed at the same time.

In one embodiment, three sets of primers, respectively targeting Gram-positive, Gram-negative, and fungal rRNA, are simultaneously used (multiplexed). Reverse transcription takes place at an appropriate temperature depending on the enzyme and on the primer annealing temperature (for example, for no more than 10 minutes). In addition, the reaction mixture may contains ingredients for performing PCR, including Taq DNA polymerase, deoxy nucleotide triphosphate mixture (dNTPs). Optionally, RNase inhibitors, Taq DNA polymerase antibody for hot-start, adjuvants to inhibit PCR inhibitors (example; bovine serum albumin) or to enhance PCR performance (example; betaine) may be included.

The PCR cycles may involve an initial incubation at 94-98° C. for 2-5 minutes, to inactivate the reverse transcription enzyme from the first stage, and to activate DNA polymerase for PCR, followed by a 2-step or 3-step thermal cycling. The thermal chamber may contain one or more specific primer sets or degenerate primers. In addition to the primers, one or more components of PCR reagent may also be provided in the chamber in a dry format, such as freeze-dried reagent, or ambient temperature dried reagent employing appropriate stabilizers.

In the example implementation illustrated in FIG. 7a, in order to perform the multiplexed detection of amplicons produced during PCR, the contents of thermal chamber 54 are transferred into plurality of wells 56 via channels 55.

In one embodiment, the detection is performed using molecular beacons. Molecular beacons have a stem-and-loop structure, with the loop portion being complementary to a single-stranded DNA target while the stem is formed by 6 to 8 nucleotides from two complementary arm sequences. A fluorophore (such as, but not limited to, fluorescein (6-FAM)) is attached to the end of one arm, while a quencher (such as but not limited to dabcyl succinimidul ester) is attached to the other arm. In the absence of the specific target, the molecular beacon remains in a "dark" state. In the presence of the specific target, the fluorophore and quencher are separated and the fluorescence emission, resulting from excitation by light with appropriate spectrum, can be detected by an optical system. In the preferred embodiment, the excitation and detection are performed using epi-fluorescence microscopic objective that may utilize an LED light source. In some embodiments, the molecular beacon may be stored in wells 56 in a solution or in dry format.

According to one example implementation, a primer pair to detect all bacterial 16S rRNA genes may be CGGCTAACTC-CGTGCCAGCAG (SEQ. ID. 1) and ATCTCTACG-CATTTCACCGCTACAC (SEQ. ID. 2), which targets a hypervariable region of target bacterial species (nucleotides 504 to 697 using Escherichia coli O104:H4 str. 2011C-3493 as a reference). A primer pair to detect target fungal species could be AGGGGGAGGTAGTGACAATAAAT (SEQ. ID. 3) and CAAAGTTCAACTACGAGCTT (SEQ. ID. 4), which targets a variable region of eukaryotic 18S rRNA (nucleotides 436 to 622 using Candida albicans AB013586 as a reference). The molecular beacons can subsequently be used to identify specific nucleotide patterns within this amplified region to distinguish between the pathogens of interest. For example, a molecular beacon designed to detect target Gram-negative species could be 6-FAM-5'-CCGAGCGGTGCAAGCGT-TAATC GGAATTACTGGGCGCTCGG-3'-DABCYL (SEQ. ID. 5), which targets a region of the 16S rRNA gene (nucleotides 541-569 using Escherichia coli O104:H4 str. 2011C-3493 as a reference) conserved in all Gram-negative bacteria. Alternatively, a molecular beacon designed to detect target fungal pathogens could be 6-FAM-5'-CCGAGCTCTGGTGCCAGCAGCCGCGGTAATTCGCT CGG-3'-DABCYL (SEQ. ID. 6), which targets a region of the 18S rRNA gene (nucleotides 539 to 564 using Candida albicans AB013586 as a reference) conserved in all fungi. Using this strategy, target bacterial and fungal blood pathogens can be identified using a small number of primer pairs and several molecular beacons. The molecular beacons could ultimately be multiplexed, allowing one to identify multiple bacterial and/or fungal pathogens in a single chamber.

Figure 8:
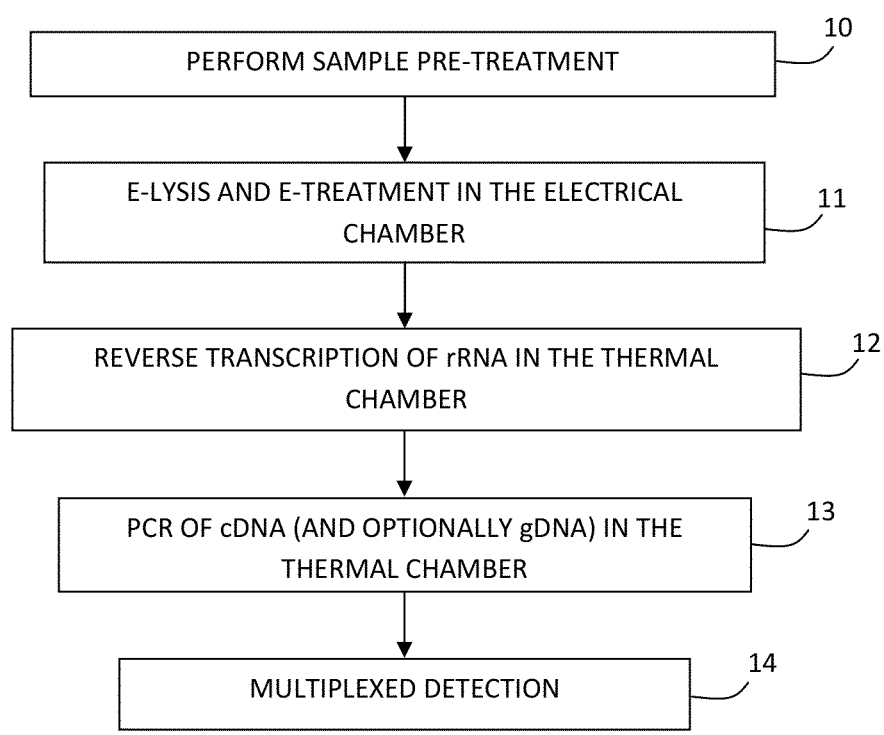
FIG. 8 provides a flow chart illustrating a method of detecting and identifying microbial cells in a whole blood sample.

Referring now to FIG. 8 a flow chart is provided that illustrates an example method of performing microbial classification and/or identification according to one embodiment. In step 10, sample pretreatment is performed according to the preceding embodiments. The result is a cell suspension in a liquid with desired composition that is appropriate for the subsequent sample treatment and nucleic acid amplification steps. The sample pretreatment step may also be useful for substantially reducing or eliminating the presence of DNA fragments from dead microbes that can be introduced while taking sample from infected patients.

Electrical processing, by which the microbial cells are lysed and the intracellular rRNA and genomic DNA are rendered accessible for external enzyme action, is performed in step 11, as described above. Electrical treatment in this step may also inactivate enzymes or factors inhibitory to subsequent amplification and detection. In step 12, the pretreated and lysed sample is mixed with an appropriate master mix in the thermal channel and targeted regions of the rRNA are reverse transcribed into corresponding cDNA. The master mix contains components for performing cycles of PCR amplification on the cDNA or specific regions of gDNA, as shown in step 13.

In the method and embodiments disclosed, the three preceding steps, namely 11, 12 and 13, are preferably performed in fluidic sequence in a single device in order to prevent or reduce losses in the number of target molecules. Such losses are associated with liquid exchanges and movements in commonly used methods for sample extraction and/or preparation. Accordingly, this aspect of the present method, along with the efficient sample pretreatment step 10, potentially enables achieving a detection limit down to a few microbial cells in the sample.

Performing an assay based on rRNA, as opposed to gDNA, as the primary mode of detection, may provide enhanced sensitivity for two reasons. Firstly, rRNA is not as stable as gDNA and thus foreign rRNA has a much smaller chance of being introduced into the thermal chamber as a major contamination component. Secondly, the number of rRNA molecules becoming available after electrical treatment of step 11, for even a single cell, is in the range of $10^4$, which, according to the methods disclosed herein, will generally exceed the quantity of contaminant background molecules.

Following the completion of step 13, the liquid contains sufficient cDNA and/or amplicons to be split into multiple aliquots and delivered into a plurality of wells, in a manner such that each well receives a statistically significant number of target molecules.

As noted above, each well may be pre-filled, optionally in dry format, with appropriate nucleic acid detection reagents. Accordingly, spatially multiplexed detection may be performed. In one embodiment, spatially multiplexed detection may be performed using molecular beacons for signal generation. In other embodiments, multiplexed detection may be performed by melting curve analysis of the amplicons stained with a double-stranded DNA dye, or employing fluorophores with different emission wavelengths.

In some embodiments, the panel of rRNA tests may be selected to enable rapid de-escalation of antibiotic therapy from one or more broad-spectrum antibiotics to one or more narrow-spectrum antibiotics. Using narrow-spectrum antimicrobial drugs not only provides a benefit in terms of cost reduction, but it also limits the potential for adverse effects such as superinfection and the development of drug-resistant microbes. As noted above, the present embodiments enable the rapid detection and/or identification of infectious agents, which could improve the decision-making process of health care professionals, and help them to administer narrow spectrum antimicrobial drugs at an earlier time. This may prevent the development of resistance, reduce toxicity, and substantially reduce healthcare costs.

Unlike known molecular methods that are focused on the targeted identification of an organism at the species level based on a comprehensive, species-level test panel, such as the Septifast system, selected embodiments described herein provide sufficient information for rapid de-escalation of antimicrobial therapy, without needing to provide full species and/or genus level identification for every expected pathogen. The reduced panels described herein are suitable for effective rapid re-vectoring of antimicrobial treatment because many organisms will respond to a common narrow-spectrum antibiotic, and as such, the test panel need not identify each and every genus and/or species of the expected pathogens, an instead need only identify those organisms or groups of organisms whose presence or absence will impact antimicrobial therapy and guide the selection of appropriate narrow-spectrum antibiotics. In many of the embodiments provided herein, a test panel is selected to provide information that is not exclusive to the genus or species level, but is instead includes a combination of rRNA test results at the kingdom, Gram-status, genus, and species levels.

Accordingly, in some embodiments, a test panel for rapid de-escalation of antimicrobial therapy includes, at a minimum, the following:

(a) one or more primary rRNA tests at the kingdom level to determine whether the organism is a bacterial or a fungal organism;

(b) one or more secondary tests to identify the Gram status of the organism, if bacterial; and (c) one or more tertiary rRNA tests, for each of fungi, Gram-positive bacteria, and Gram-negative bacteria, to identify at least one genus or species of the organism, where the result of the tertiary test is suitable for selecting an appropriate narrow-spectrum antibiotic.

In some embodiments, one or more of the rRNA tertiary tests may be replaced and/or augmented by a strain level test, where the strain level test may be a gDNA test suitable for identification of a selected strain.

It has been found that such test panels are sufficient for rapid de-escalation of antimicrobial therapy from broad spectrum antibiotics to narrow spectrum antibiotics, especially when the test is performed on a direct, non-enriched sample, prior to enrichment or culturing.

The selection of one or more tertiary tests at the species or genus level will depend on a number of factors, such as the nature of the antibiogram, and the availability of suitable antibiotics. Non-limiting examples of test panels are described below. For example, over time, a suitable genus or species level tertiary test for Gram-negative bacteria may change due to changes in pathogen prevalence, changes in antibiotic resistance, and/or the availability of new antibiotics.

In some embodiments, the reduced test panel is selected by mapping the available antibiotics to information associated with the highest levels of pathogenic taxa, and the test panel is selected to include the tests for these highest levels. For example, the test panel may include, at a high level, three multiplex tests for isolating a true positive sample to one of Gram-positive, Gram negative, or fungi. This may be achieved, as noted above, by isolating specific regions of the ribosome belonging to all Gram-positive bacteria, to the exclusion of all others, for example, it becomes possible to identify a true Gram-positive sample. If this same procedure is repeated for all Gram-negative bacteria to the exclusion of all others, it becomes possible to identify a true Gram-negative sample. A third test would isolate and identify a true fungal sample.

This reduction principle may be repeated in a hierarchical format (for example, a decision tree or a flow chart) to determine the set of tests needed to de-escalate antimicrobial therapy. This effectively reduces the very large number of tests for all possible organisms to a subset of tests relevant to antimicrobial re-vectoring.

For example, a suitable test panel may involve a kingdom-based primary test for bacterial vs. fungal organisms, a Gram-status secondary test, and a tertiary test for the genus of Streptococci, and an additional species-level tertiary test, provided that the species-level test would enable further antimicrobial de-escalation. For example, a species-level tertiary test for *Streptococcus pneumoniae* would enable further de-escalation, based on presently available antibiotics.

In another example, a suitable tertiary test may be for the genus of *Staphylococcus*, and the test panel may include an additional species-level tertiary test for the species of *Staphylococcus aureus*. A sample testing positive to both of these tertiary tests would be thought to include *Staphylococcus aureus*, and a medical practitioner could subsequently decide to de-escalate antibiotic therapy to Vancomyacin and Oxacillin due to the awareness of potential methicillin resistance. On the other hand, if the sample found to be positive to Gram-positive and *Staphylococcus*, but negative to *S. aureus*, then the medical practitioner may determine that the offending organism is probably Staphylococci other than *S. aureus* and most probably a contaminant, which could lead the medical practitioner to determine that treatment is not warranted.

This principle is illustrated in FIGS. 9(a) and 9(b). In FIG. 9(a), a hierarchical panel diagram is shown in which the number of tests that determines a course of antimicrobial therapy for blood infections has been reduced to nine. FIG. 9(b) shows an example of organism identification based on different possible panel test results, along with a corresponding determination of a suitable antibiotic. Such a panel is important in at least two respects. Firstly, the number of tests is significantly reduced, compared to species-level test panels. For example, there are well over 100 possible sources of bacterial or fungal infections, and testing for each and every one would be an arduous and complicated task, making a rapid diagnosis and targeted treatment difficult. Secondly, the degree of confidence with each hierarchical level in the panel tree is increased, which could very possibly impact treatment decisions on a real-time basis. This approach, in effect, has a built-in control that improves the confidence interval.

Figure 10A:
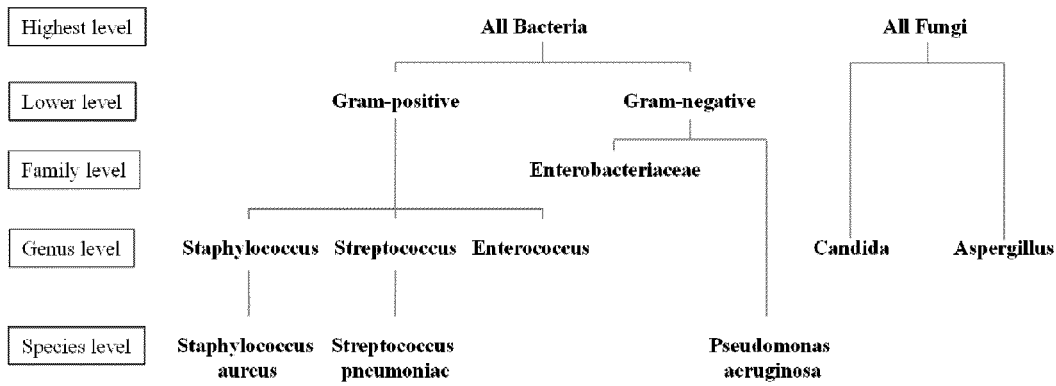
FIGS. 10(a)-10(c) illustrate three example rapid identification panels for de-escalation of antibiotic therapy from broad-spectrum antibiotics to narrower spectrum antibiotics.
Figure 10B:
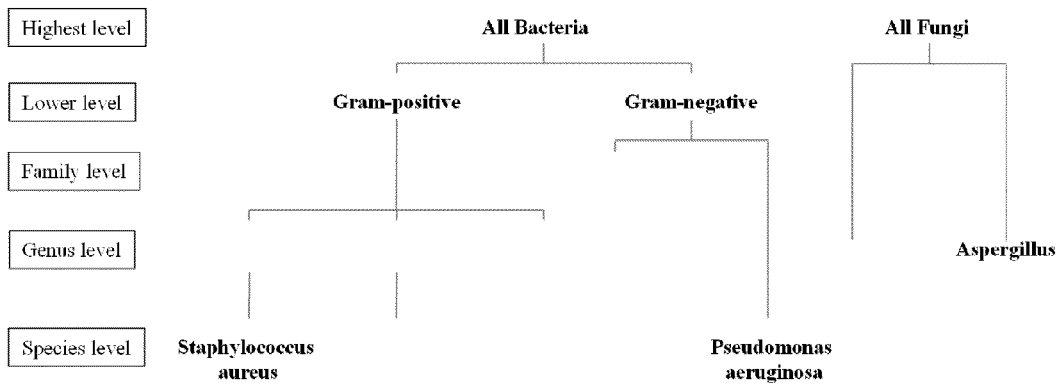
Figure 10C:
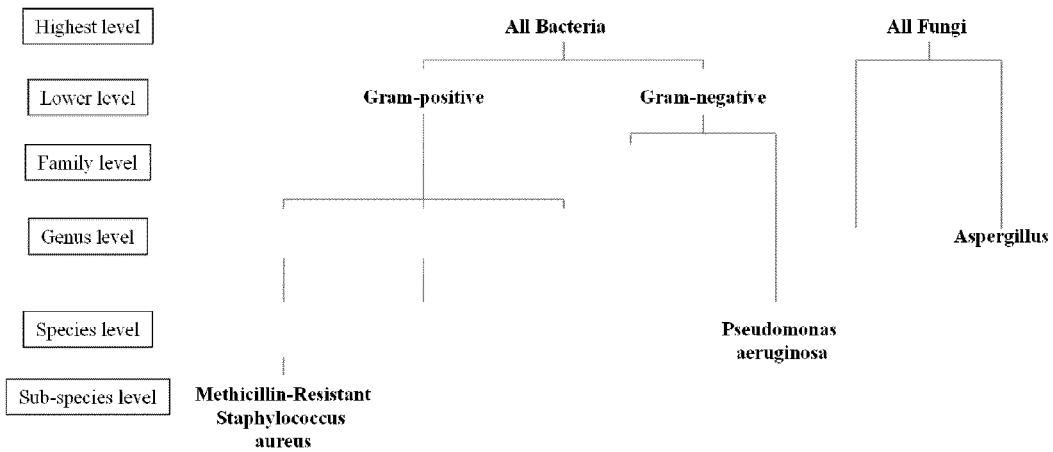

Three additional example panels are presented in FIGS. 10(a) through (c). The panel shown in FIG. 10(a) provides the following information: an indication of the kingdom classification (bacterial or fungal) of the pathogen, the Gram status of a bacteria, and further identification of selected genus and/or species levels. As noted above, identification of pathogens at a family and/or genus level may assist in decision making for antimicrobial drug selection and further testing as necessary. In this example panel, identification of selected pathogens at a species level provides the physician with specific information that is relevant to de-escalation of antimicrobial treatment, and information that can warrant further testing. For example, the identification of S. aureus at the species level could indicate to the physician that further testing for MRSA is warranted. Also, for example, the identification of S. pneumoniae at species level could alarm the physician to increasing ampicillin-resistant strains of S. pneumoniae. Furthermore, the identification of P. aeruginosa at species level could support a decision to alter the antimicrobial therapy to a more targeted, narrow-spectrum antimicrobial drug that is more selective for P. aeruginosa. Similarly, identification of Aspergillus can assist decision-making for more appropriate and narrow-spectrum treatment, while other fungi are generally sensitive to wider spectrum antimycotic agents.

In the panel shown in FIG. 10(b), pathogen information is provided at the family, genus and/or species level in a more selective manner that is correlated with the selection of narrow-spectrum and appropriately targeted antimicrobial therapy. This panel is formulated based on the assessment that other than S. aureus, similar antibiotics can be considered for other Gram-positive bacteria. As a result, the S. aureus species level test is sufficient to provide suitable information for de-escalation of antibiotic therapy if the pathogen is found to be Gram-positive. Furthermore, if S. aureus is identified, the physician may request a test known for the mecA gene in order to determine whether or not the pathogen is MRSA. As noted above, the detection and identification for the panels shown in FIGS. 10(a) and 10(b) may be performed by detecting specific nucleic acid sequences within the pathogen's rRNA.

In the example panel shown in FIG. 10(c), the mecA gene a strain level test is provided for the detection of MRSA, which renders the species level test for S. aureus unnecessary. The test for the mecA gene may performed based on the detection of genomic DNA. If the pathogen is found to be Gram-positive but not MRSA, then suitable other antibiotics which can cover all Gram-positive pathogens can be considered for treatment.

The aforementioned rapid sample pretreatment and rRNA-based testing protocols, when combined with a rapid de-escalation test panel as described above, enables the rapid and effective selection of appropriate narrow-spectrum antibiotics, or the appropriate initial selection of a suitable antibiotic, thereby dramatically reducing the number of tests, and the complexity of medical inquiry, required to enable a therapeutic decision. In particular, when aforementioned methods of sample pretreatment and rapid rRNA reverse transcription PCR are employed to perform tests according to such a rapid de-escalation panel, results are provided on a suitable timescale to affect patient outcomes, and with sufficient information to guide the de-escalation of antimicrobial therapy.

As noted above, the present embodiments do not require an enrichment step, and are capable of rapidly providing results that influence antimicrobial treatment. For example, in some embodiments, the time delay between initiating the pretreatment phase and the availability of the test results may be less than approximately 30 minutes. The rapid availability of the test results is important for enabling de-escalation of antimicrobial treatment, or prescribing an initial narrow-spectrum antibiotic, on a clinically relevant and effective timescale.

This is to be contrasted with existing molecular methods, which fail to find widespread clinical utility due to (1) the requirement for complex and time consuming manual sample preparation steps, (2) insufficient recovery of microbial cells when performing sample preparation based on direct, non-enriched samples, and (3) overly complex test results that fail to clearly inform appropriate decision making in antimicrobial stewardship.

The following examples are presented to enable those skilled in the art to understand and to practice embodiments of the present disclosure. They should not be considered as a limitation on the scope of the present embodiments, but merely as being illustrative and representative thereof.

EXAMPLES

In the following examples, Gram-negative bacteria cells were grown on LB agar plates and a single colony of cells was cultured in LB broth overnight at 37° C. Gram-positive bacterial and fungal cells were grown on tryptic soy agar with 5% sheep blood and a single colony of cells was cultured in tryptic soy broth overnight at 37° C. The cells were centrifuged at 7000 rpm for 5 min. The cell pellet was washed twice and re-suspended in 0.8 mM phosphate buffer pH 7.4, pre-filtered through a 0.2 µm filter.

The blood cell lysis reagent was used whenever blood sample pretreatment was required. The blood cell lysis reagent consisted of a mixture of saponin (84510, Sigma), sodium polyanethol sulfanate (SPS) (P2008, Sigma) and poly (propylene glycol) (PPG) MW 2000 (202339, Sigma). Saponin was dissolved in reagent grade water, filtered through 0.2 µm PES syringe filter and purified using Amicon Ultra-15 10K MW cut-off (Z706345, Sigma). SPS was dissolved in reagent water and filtered through 0.2 µm PES syringe filter. PPG MW 2000 (202339, Sigma) was used directly from the original bottle. In addition, Fluorinert™ FC-40 (F9755, Sigma) was added to serve as sedimentation liquid.

The following standard procedure is performed in experiments which required pretreatment of blood samples, unless any variation is specified otherwise. 10 µL of Fluorinert™ was added to 2 mL siliconized microcentrifuge tubes (Sigma), followed by the addition of 500 µL of the blood cell lysis reagent. The blood cell lysis reagent consisted of 75 mg/mL saponin, 15 mg/mL SPS and 1% PPG. Sodium citrate-treated human whole blood (Bioreclemation Inc.) spiked with microbial cells was added to the tube containing the blood cell lysis reagent and the Fluorinert, and mixed by inverting ten times and vortexing at low speeds for 10 sec. The final concentrations of the components in the mixture were 25 mg/mL saponin, 5 mg/mL SPS and 0.33% PPG. The tubes were centrifuged at 12,000 rpm for 1 min. Most of the supernatant was removed, leaving 150 uL of the liquid supernatant, Fluorinert and the sedimented microbial cells. Four wash cycles were performed by re-suspending in 0.8 mM phosphate buffer, mixing by inverting 10 times, vortexing at low speed for 10 sec, centrifugation at 12,000 rpm for 1 min and removal of the supernatant, leaving 150 µL of the liquid supernatant, the Fluorinert and the sedimented microbial. After the last wash, most of the supernatant is removed and the sedimented microbial cells were re-suspended in respectively specified volume of 0.8 mM phosphate buffer pH 7.4, and the sample is designated as the pretreated sample. Positive control samples are prepared by spiking 0.8 mM phosphate buffer pH 7.4 with the same concentration of respective microbial cells as the nominal concentration of the pretreated sample in respective experiments.

In examples that required electrical cell lysis, the pretreated samples and the positive control samples were passed through an electrical chamber with steps of 10 µL/10s and applying n=250 bipolar square pulses having duration of 50

μs and amplitude of 190 V. The electrical chamber had a dimension of 6.4×15×0.2 mm$^3$ and the inlet and outlet ports were of restricted type.

In the following examples, real-time reverse transcription PCR (real-time RT-PCR) assay was performed to detect a specific target region in 16S or 18S rRNA of respective microbial cell types. The primers were designed by sequence alignment software (Bioedit, Ibis Biosciences, USA) and primer design software (Primer3, National Institutes of Health). The cell lysate of the pretreated sample and the spiking control following the electrical lysis was subjected to real-time RT-PCR. In addition to the samples, the following negative controls were subjected to real-time RT-PCR: pre-filtered phosphate buffer used for cell suspension (negative control; buffer), and unspiked blood subjected to the same pretreatment and electrical lysis protocol as the spiked blood samples (negative control; blood).

Unless any variation was specified, RT-PCR reaction of 204 volume was prepared by mixing 5 μL of sample, 10 μL of Kapa 2G Robust Hotstart 2×PCR reaction mix (kk5515, KAPA Biosystems), 1.24 of reverse transcriptase (GoScript, A500z Promega), 1 μL of forward primer (10 μM), 14 of reverse primer (10 μM), 1 μl of SYTO-9 (100 nM, S34854, Invitrogen) and 0.8 μL of RNAase free water. One-step real time RT-PCR was performed by reverse transcription at 55° C. for 5 min, inactivation of reverse transcription at 95° C. for 2 min, followed by 35 cycles of cDNA amplification (denaturation at 95° C. for 3 sec, annealing at respective temperature for 3 sec, and extension at 72° C. for 3 sec) in Eco Real Time PCR system (illumina) using a double stranded DNA binding fluorescent dye, SYTO-9.

Example 1

The Requirement on the Number of Wash Steps to Eliminate Inhibitory Effects of Lysed Blood Debris on Molecular Assays The experiments presented in this example were performed to demonstrate how washing cycles and electrical treatment reduces the inhibitory effects of the lysed blood debris on the downstream molecular assays. The dependence of a typical RT-PCR assay on the number of washing cycles during the sample pretreatment was tested.

NEB 5-alpha laboratory strain *Escherichia coli* cells were used and the cell suspension, prepared as described above, was diluted to the cell concentration of 2000 CFU/mL. In this example, the cells were lysed by heating the suspension at 95° C. for 10 minutes.

Human whole blood was subjected to the sample pretreatment procedure as described above and either three or four wash cycles were performed. After the last wash, most of the supernatant was removed and any sediment (blood dcell debris) was re-suspended in 120 μL of 0.8 mM phosphate buffer pH 7.4. Each suspension was split into two aliquots, one was not treated, but the other was electrically treated by passing through an electrical chamber as described above. The treated or untreated sample of 60 μL was mixed with 15 μL of the 2000 CFU/mL bacterial cell lysate prepared by heating as described. The resulting 75 μL samples included the equivalent of 30 lysed microbial cells and 5 μL of each sample containing the equivalent of 2 lysed microbial cells was assayed with real-time RT-PCR. The forward and reverse primers used for RT-PCR were GTGCCCTGAGGCGTG-GCTTC (EnterobF2) and GCGGGACTTAACCGAACAT-TCAC (EnterobR2), respectively, targeting all Enterbacteriaceae species. The 16S rRNA gene fragment of 252 bases pair at a conserved region of all enterobacteraciae (nucleotides 830 to 1082 using *Escherichia coli* O104:H4 str. 2011C-3493 as a reference) was amplified.

Figures 11A, 11B:
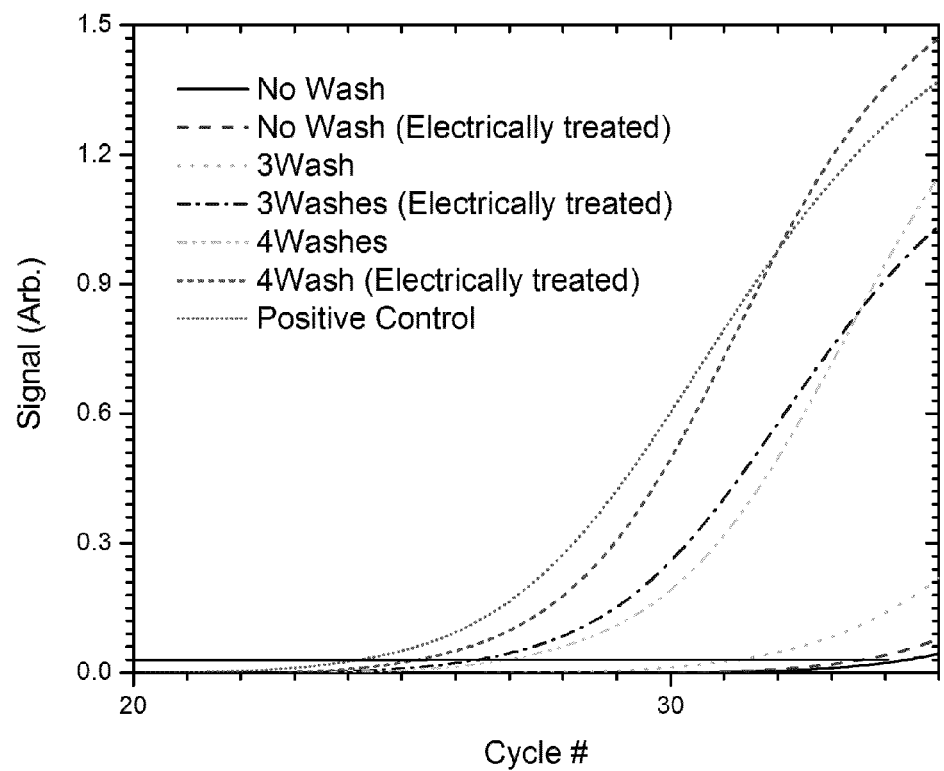
FIG. 11(a) shows the fluorescence signal versus cycle number measured during real time PCR assays, illustrating the dependence of the assay signal on the number of wash steps and electrical treatment.

The resulting signal versus cycle # plots is presented in FIG. 11a. The $C_T$ values were determined at a signal level of 0.1 and summarized in FIG. 11b. As it is observed electrical treatment greatly reduces the inhibitory effects of blood debris by an amount that is at least equivalent to one extra wash cycle. In other words, the effects of electrical treatment in reducing the inhibitory effects of blood lysis debris, is equivalent to diluting inhibitors by a factor of 13. Moreover, in the case of the RT-PCR reagents used in the present tests, 4 washes are barely sufficient for eliminating the inhibitory effects of blood debris.

Example 2

Dependence of Microbial Cell Recovery on the Pretreatment Mixture Composition and Pretreatment Vessel Interior Surface The experiments presented in the following examples were performed to demonstrate the efficiency by which the microbial cells in a whole blood sample are recovered into the pretreated sample and that molecular assay inhibitory compounds are removed or inactivated. As noted above, such methods may be applicable for downstream reagentless microbial cell lysis followed by a nucleic acid assay without requiring additional steps of nucleic acid extraction/purification and/or medium balance. The dependence of microbial cell recovery on blood cell lysis reagent composition, volume of cushioning liquid and interior surface property of the sample pretreatment vessel were verified.

In these experiments, the viability of the recovered microbial cells may not be of concern, which is in contrast to cases when microbial cells are intended for subsequent growth (such as in the disclosures of Dorn referenced above). Instead, it may be sufficient that the blood cell lysis reagent does not substantially damage the microbial cells, to the extent of releasing nucleic acids and other macromolecules of interest, and avoids the introduction of nucleic acid assay inhibitory agents in the pretreated sample. Accordingly, the blood cell lysis reagent composition may be selected such that it is appropriate for wide range of microorganisms, in particular Gram-negative bacteria that are less tolerant of strong blood cell lysis agents. In order to demonstrate the capability of the method for the preparation of such less tolerant bacteria, the following examples were performed with *Pseudomonas aeruginosa* as the test organism.

*P. aeruginosa* cells were cultured and the cell suspension was prepared as described above. 10 μL of Fluorinert™ was added to 2 mL siliconized microcentrifuge tubes, followed by the addition of 500 μL of the blood cell lysis reagent. The blood spiked with *P. aeruginosa* in 1 mL volume at 600 CFU/mL was added to the tube containing the blood cell lysis reagent and the Fluorinert and mixed by inverting 10 times and vortexing at low speeds for 10 sec. The sample pretreatment was performed as described above. After the last wash, most of the supernatant was removed and the sedimented cells were re-suspended in 300 μL of 0.8 mM phosphate buffer pH 7.4. The resulting pretreated sample contained a nominal cell number of 600. A 60 μL volume of the pretreated samples and the positive control were lysed by electrical lysis as described above. 5 μL of the cell lysate, containing the equivalent of 10 lysed microbial cells, and the negative control were assayed with real-time RT-PCR. The forward and reverse primers used for RT-PCR were GGGCAGTAAGT- TAATACCTTGC (PAF1) and TCTACGCATTTCACCGC-TACAC (PAR1), respectively. The 16S rRNA gene fragment of 251 bases pair at a conserved region of *P. aeruginosa* (nucleotides 438 to 689 using *Pseudomonas aeruginosa* D77P as a reference) was amplified.

Blood cell lysis reagent with varying concentrations of saponin and SPS, and varying volumes of Fluorinert™ were tested to verify the significance of each component in the pretreatment mixture. Then, using the optimized composition of the pretreatment mixture, bacteria recovery from pretreatment vessels with or without interior surface treatment was investigated.

Example 2.1

The Effects of Saponin Concentrations on Real-Time RT-PCR Assay Signal

Figure 12:
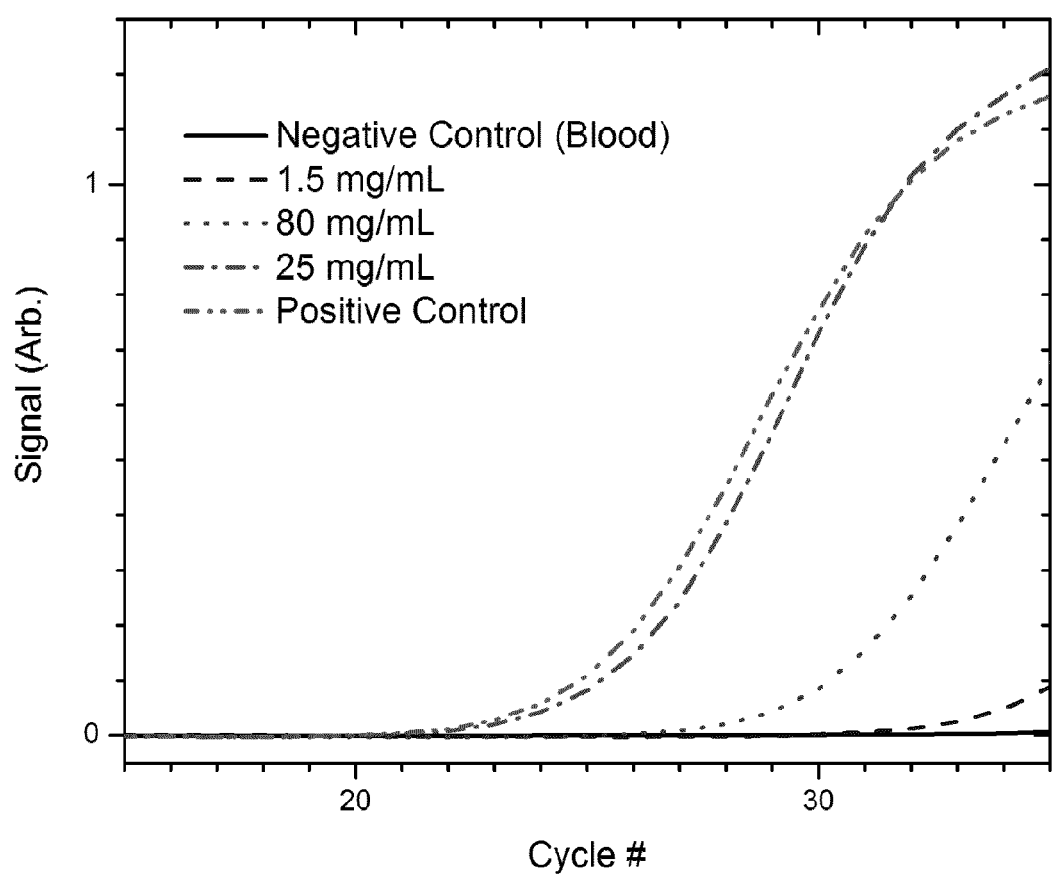
FIG. 12 shows the fluorescence signal versus cycle number measured during real time PCR assays, illustrating the dependence of the assay signal on the concentration of saponin.

Human whole blood of 1 mL, spiked to 600 CFU/mL *P. aeruginosa* was added to 0.5 mL of the pretreatment mixture containing 10 µL of Fluorinert™ FC-40, 4.5 to 240 mg/mL saponin, 15 mg/mL SPS and 1% PPG, in a 2 mL siliconized microcentrifuge tube. The final concentrations of the components in the mixture were 1.5 to 80 mg/mL saponin, 5 mg/mL SPS and 0.33% PPG. The sample pretreatment procedure was performed and the pretreated samples and positive controls were electrically lysed. The real time RT-PCR assay signal of the bacteria in the pretreated sample recovered from the whole blood after the sample pretreatment is presented in FIG. 12. It appears that a final concentration of saponin of approximately 25 mg/mL is the most effective concentration for the present experimental conditions.

Example 2.2

Variation in Concentrations of SPS on Real-Time RT-PCR Assay Signal

Figure 13:
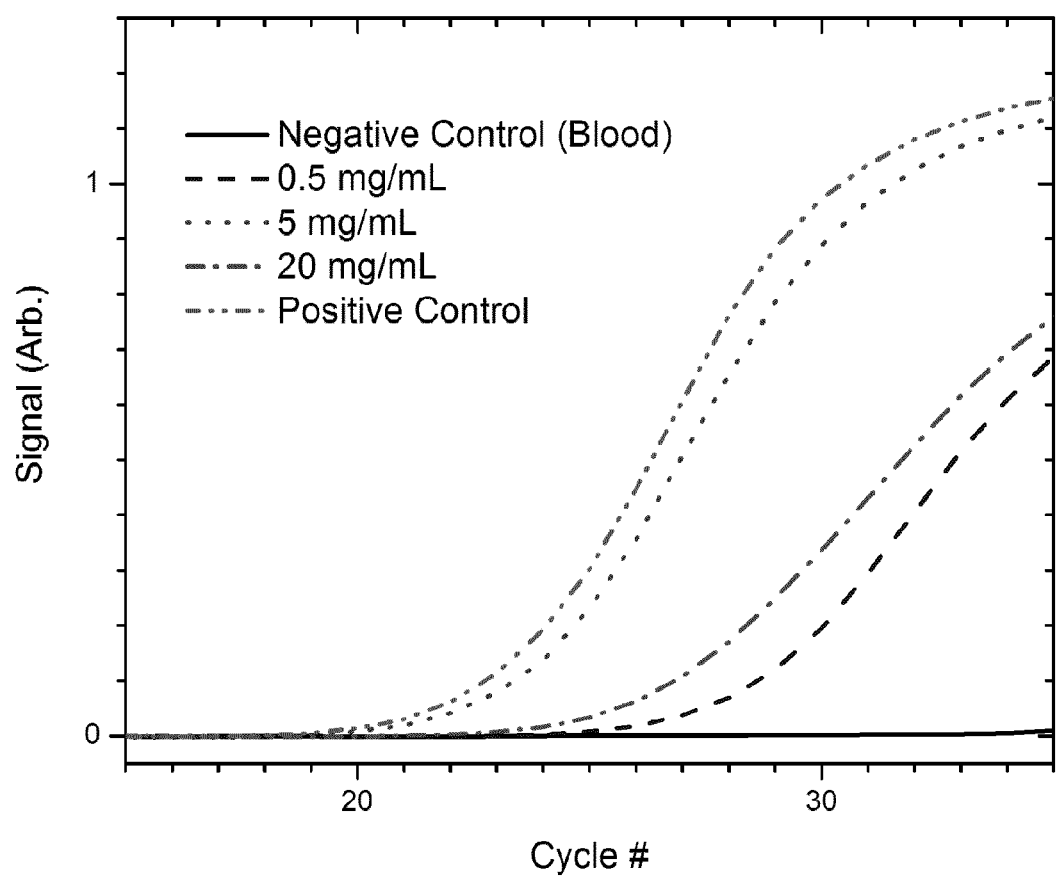
FIG. 13 shows the fluorescence signal versus cycle number measured during real time PCR assays, illustrating the dependence of the assay signal on the concentration of SPS.

Human whole blood of 1 mL, spiked at 600 CFU/mL *P. aeruginosa* was added to 0.5 mL of the pretreatment mixture containing 10 µL of Fluorinert™ FC-40, 75 mg/mL saponin, SPS in the range of 0.5-20 mg/mL and 1% PPG, in 2 mL siliconized microcentrifuge tube. The final concentrations of the components in the mixture were 25 mg/mL saponin, 0.5 to 20 mg/mL SPS and 0.33% PPG The real time RT-PCR assay signal of the bacteria in the pretreated sample recovered from the whole blood after the sample pretreatment is presented in FIG. 13. It appears that a final concentration of SPS of approximately 5 mg/mL is the most effective concentration for the present experimental conditions.

Example 2.3

Variation in Volumes of Fluorinert™ on Real-Time RT-PCR Assay Signal

Figure 14:
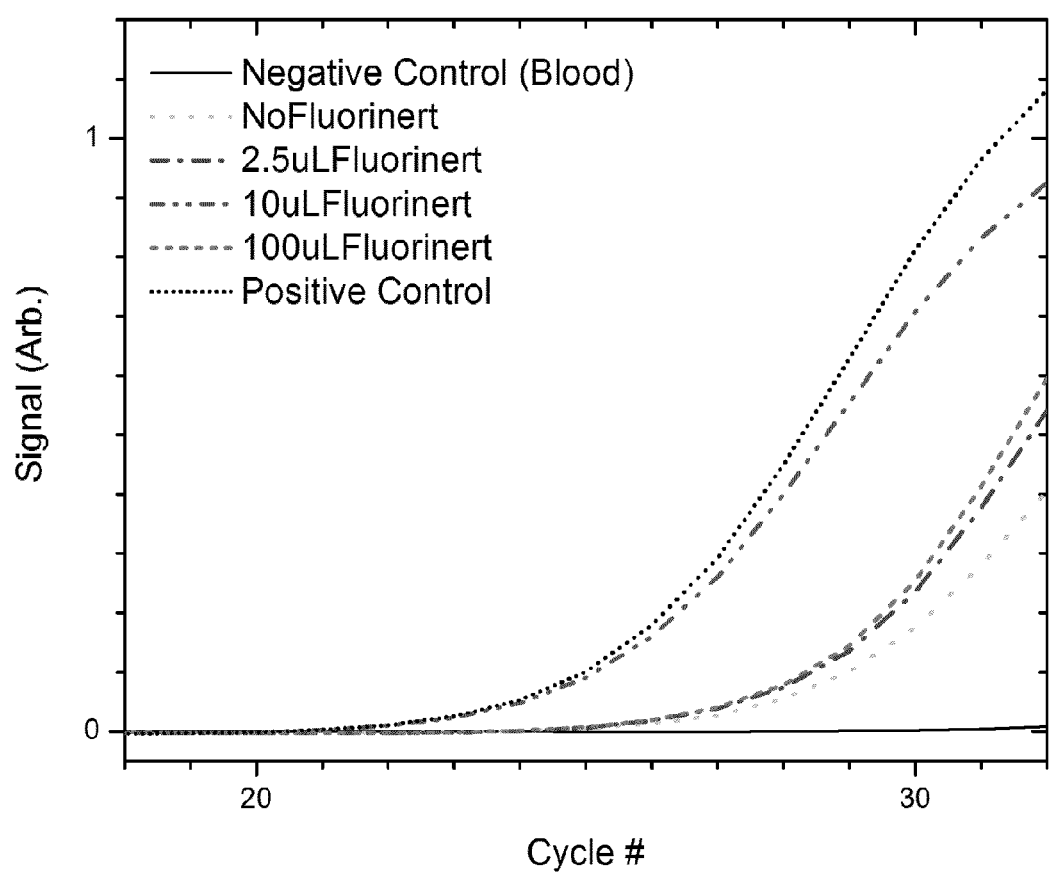
FIG. 14 shows the fluorescence signal versus cycle number measured during real time PCR assays, illustrating the dependence of the assay signal on the volume of Fluorinert™.

Human whole blood of 1 mL, spiked at 600 CFU/mL *P. aeruginosa* was added to 0.5 mL of the pretreatment mixture containing different volumes of Fluorinert™ FC-40, 75 mg/mL saponin, 15 mg/mL SPS and 1% PPG, in 2 mL siliconized microcentrifuge tubes. The final concentrations of the components in the mixture were 25 mg/mL saponin, 5 mg/mL SPS and 0.33% PPG. The pretreatment procedure was performed and the samples were electrically lysed. The real time RT-PCR assay signal of the bacteria in the pretreated sample recovered from the whole blood after the sample pretreatment is presented in FIG. 14. It was demonstrated that for the present experimental condition the volume of Fluorinert should be more than 2.5 µL and less than 100 µL.

Example 2.4

Figure 15:
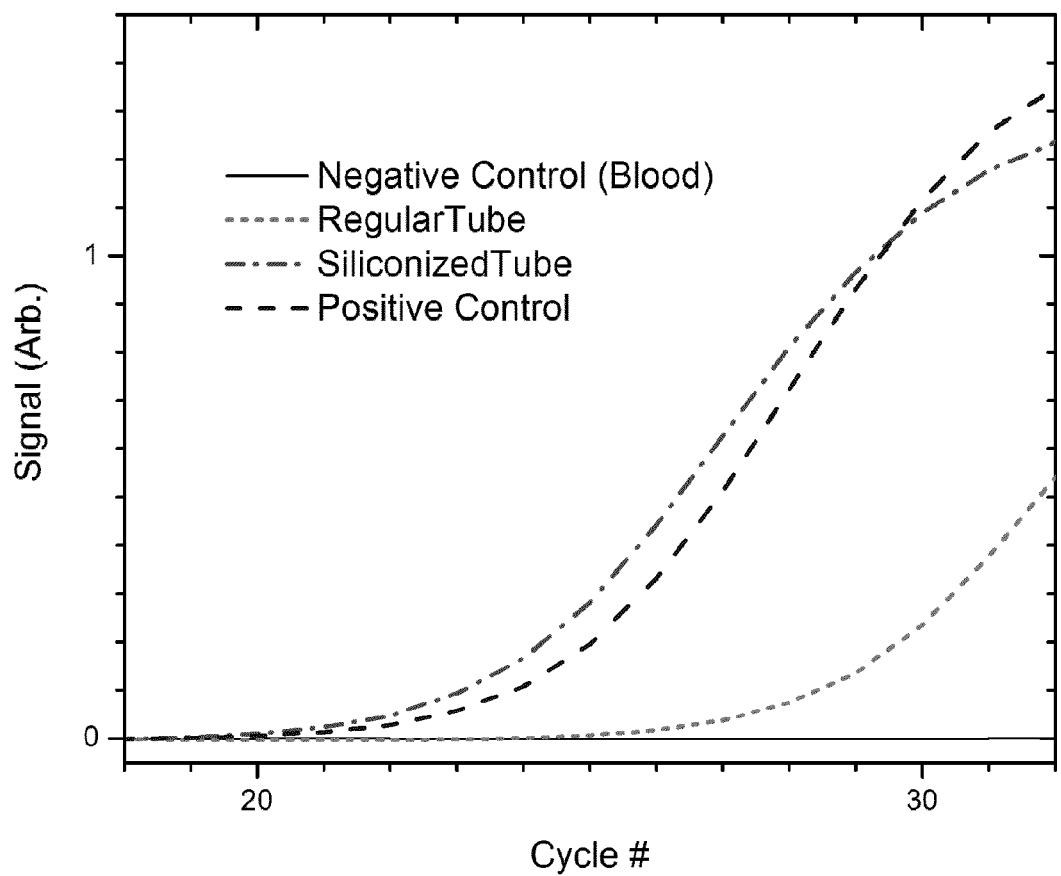
FIG. 15 shows the fluorescence signal versus cycle number measured during real time PCR assays, illustrating the dependence of the assay signal on the pretreatment vessel surfaces.

Variation in Pretreatment Vessel Interior Surface Property on Real-Time RT-PCR Assay Signal Human whole blood of 1 mL, spiked at 600 CFU/mL *P. aeruginosa* was added to 0.5 mL of the pretreatment mixture containing 10 µL of Fluorinert™ FC-40, 75 mg/mL saponin, 15 mg/mL SPS and 1% PPG, in 2 mL microcentrifuge tube with or without interior surface treatment. In one group, regular 2 mL polypropylene microcentrifuge tubes (B71420, Bioplastics) were used. In the other group, 2 mL siliconized microcentrifuge tubes (T-3531, Sigma) were used. The final concentrations of the components in the mixture were 25 mg/mL saponin, 5 mg/mL SPS and 0.33% PPG. The real time RT-PCR assay signal versus cycle number of the bacteria in the pretreated sample recovered from whole blood after sample pretreatment is presented in FIG. 15. The $C_T$ value for regular tube is about 4 cycles later than the case of siliconized tube, indicating more efficient cell recovery during the pretreatment process. Therefore, the siliconization of the interior surface is required for more efficient recovery of bacterial cells from the whole blood.

Example 3

Detection Limit of Microorganisms Spiked in Human Whole Blood

The three examples presented in this section demonstrate the ability of the device to detect microbial cells in human whole blood with a detection limit in the range of 1-10 cells per mL for fungi, Gram-positive bacteria and Gram-negative bacteria.

Human whole blood (Bioreclemation Inc.) of 1 mL volume was spiked with the microbial cells specific to each example below and subjected to pretreatment and electrical lysis as described above. As a positive control, the same concentration of the microbial cells in 0.8 mM phosphate buffer was subjected to electrical lysis without pretreatment.

Human whole blood of 1 mL spiked with 300 and 30 CFU/mL of microbial cells was added to the tube containing blood cell lysis reagent and Fluorinert, and the standard sample pretreatment procedure was performed.

After the last wash, the supernatant was removed and the sedimented cells were re-suspended in 300 µL of 0.8 mM phosphate buffer pH 7.4 (resulting in a nominal concentration of $10^3$ and $10^2$ CFU/mL).

A 60 µL volume of the pretreated samples and the positive controls were subjected to electrical lysis. In each case, a cell lysate volume of 10 µL (nominally 10 and 1 cells respectively per sample) was subjected to amplification by RT-PCR.

In the following examples, RT-PCR reaction mixture of 25 µL volume was prepared by mixing 10 µL of sample, 12.5 µL of 2×PCR reaction mix (2G Robust HotStart, KAPA Biosystems), 1.3 µL of reverse transcriptase (GoScript, Promega), 0.6 µl of forward primer (10 µM) and 0.6 µL of reverse primer (10 µM). One-step real time RT-PCR was performed by reverse transcription at 55° C. for 5 min, inactivation of reverse transcription at 95° C. for 2 min, followed by 35 cycles of cDNA amplification (denaturation at 95° C. for 3 sec, annealing at 55° C. for 3 sec, and extension at 72° C. for 3 sec) and final extension at 72° C. for 1 min in Eco Real-Time PCR System (illumina). The resulting RT-PCR product of 15

µL was resolved by gel electrophoresis on 1% agarose gel in 0.5×TBE buffer and 0.5 µg/mL ethidium bromide at 150 volts for 30 min. The specific nucleotide sequences within the amplified region were detected using specific molecular beacon. RT-PCR product of 5 µL was mixed with 1 µL of the buffer containing 20 mM Tris-HCl pH 8, 10 mM KCl and 7 mM $MgCl_2$ as well as 1 µM of molecular beacon The mixture was heated at 95° C. for 30 sec to denature the amplicon and the molecular beacon, followed by cooling to room temperature, allowing hybridization of the molecular beacon to the target sequence. The resulting mixture of 6 µL was transferred to a micro-well and the fluorescence intensity of excitation at 492 nm and emission at 517 nm was measured using fluorescence microscopy (LumaScope, etaluma).

Example 3.1

Detection of Fungi Spiked in Human Whole Blood

Samples spiked with *C. albicans* were prepared and processed as described above for RT-PCR assay. The one-step RT-PCR protocol used UFF3 forward primer (5'-AAC-GAAAGTTAGGGGATCGAAG-3') (SEQ. ID. 15) and UFR3 reverse primer (5'-CTTTAAGTTTCAGCCTTGCGA-3') (SEQ. ID. 16). The 18S rRNA gene fragment of 167 bases pair at a hypervariable region of all fungi species (nucleotides 940 to 1107 using *Candida albicans* AB013586 as a reference) was amplified.

Figure 16:
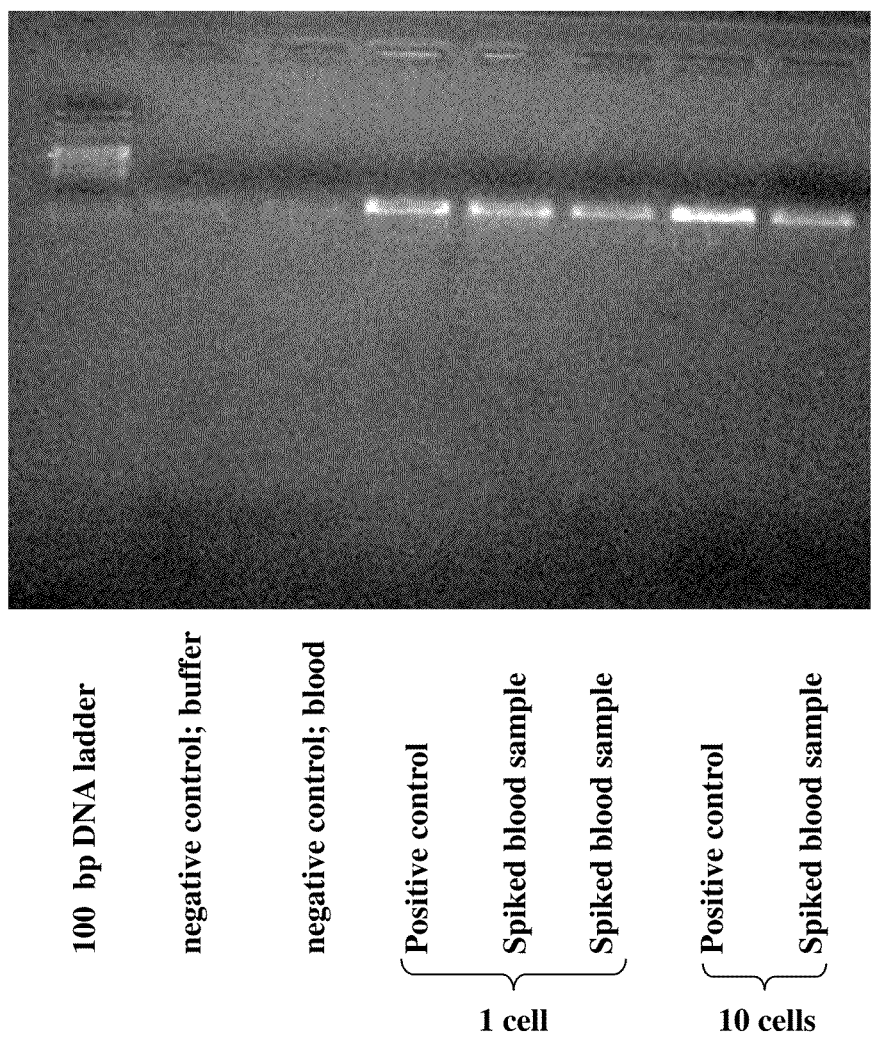
FIG. 16 demonstrates the detection limit of *Candida albicans* in blood samples. Reverse transcription PCR amplified product of the 18S rRNA fragment of *C. albicans* was visualized after resolving on agarose gel electrophoresis, showing the detection of 1 and 10 *C. albicans* cells.

The resulting RT-PCR product of 15 µL was resolved by gel electrophoresis and the amplified region of 18S rRNA was observed in FIG. 16. This example demonstrates the detection of *C. albicans* fungal cells spiked in human whole blood with sensitivity in the range of 1-6 cells.

The specific nucleotide sequences within the amplified region were detected using the molecular beacon 6-FAM-5'-CCGAGCCGTAGTCTTAACCATAAACTATGCGCT-T-DABCYL (SEQ. ID. 17) (nucleotides 977 to 997 using *Candida albicans* AB013586 as a reference), designed to detect all fungal pathogens. The detection signals of the positive controls and the spiked blood samples recovered from blood pretreatment are presented in FIG. 17. This example demonstrates the efficiency of molecular beacon method to detect *C. albicans* spiked in human whole blood with sensitivity in the range of 1-6 cells.

Example 3.2

Detection of Gram-Positive Bacteria Spiked in Human Whole Blood

Samples spiked with *S. pneumoniae* were prepared and processed as described above for RT-PCR assay. The one-step RT-PCR protocol used Ubea primer pair (UbeaF forward primer; 5'-GACAGGTGGTGCATGGTTGTC-3' (SEQ. ID. 18) and UbeaR reverse primer, 5'-ACGTCATCCCCACCT-TCCTC-3') (SEQ. ID. 19) and GP1 primer pair (GP1F forward primer; 5'-ATGCATAGCCGACCTGAGAG-3' (SEQ. ID. 11) and GP1R reverse primer; 5'-AGTTAGCCGTSS-CTTTCTG-3') (SEQ. ID. 12). The 16S rRNA gene fragment of 170 bases pair at a hypervariable region of all bacterial species (nucleotides 1035 to 1185 using *Streptococcus pneumonia* G54 as a reference) was amplified by universal bacterial Ubea primer pair and the 16S rRNA gene fragment of 230 base pairs at a hypervariable region of all Gram-positive bacterial species (nucleotide 290 to 520 using *Staphylococcus aureus* NR 037007 as reference) was amplified by Gram-positive specific GP1 primer pair.

Figure 18:
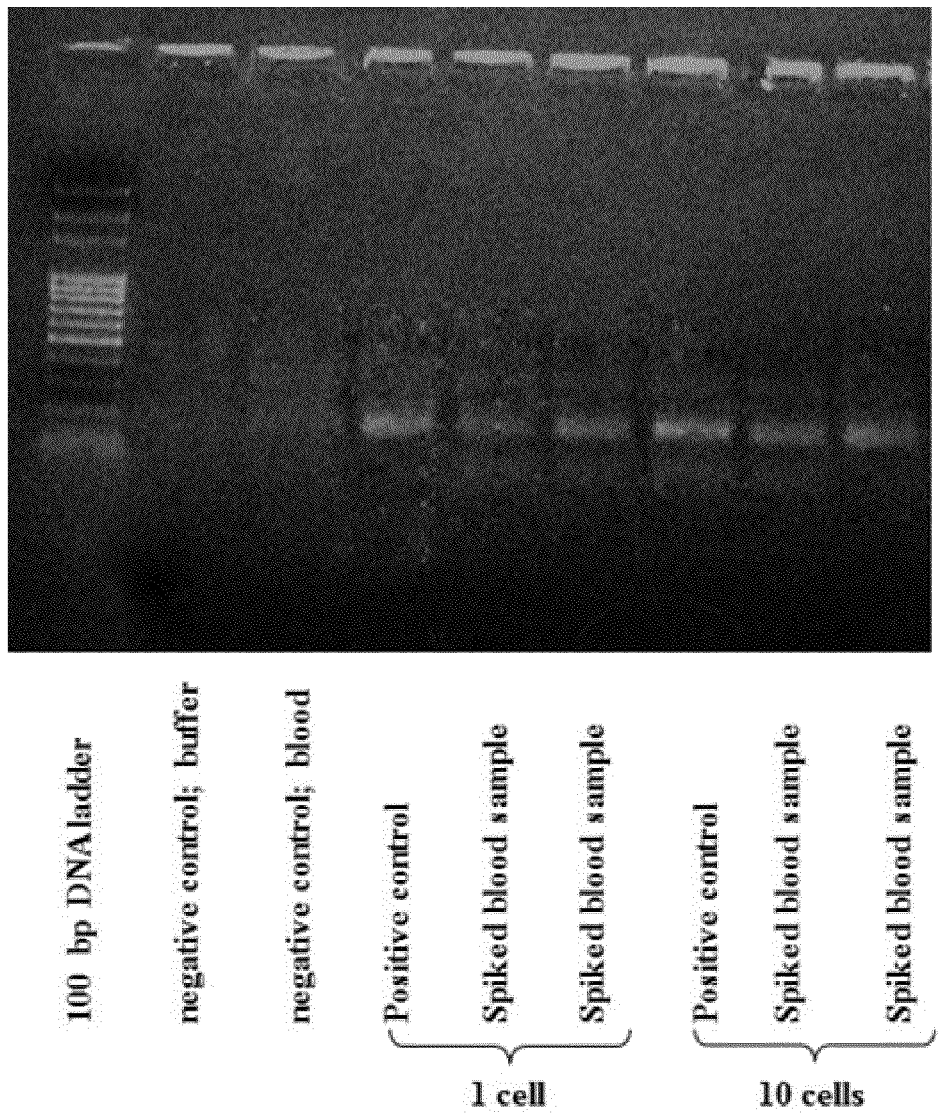
FIG. 18 demonstrates detection limit of *Streptococcus pneumoniae* in blood samples. Reverse transcription PCR amplified product of the 16S rRNA fragment of *S. pneumoniae* was visualized after resolving on agarose gel electrophoresis, showing the detection of 1 and 10 *S. pneumoniae* cells.

The resulting amplified product using GP1 primer pair, targeting all Gram-positive bacterial species was resolved by gel electrophoresis and the amplified fragment of 16S rRNA was observed in FIG. 18. This example demonstrates the detection of Gram-positive *S. pneumoniae* bacteria in blood with sensitivity in the range of 1-6 cells.

The Gram-positive specific nucleotide sequences within the amplified product using Ubea universal bacterial primer pair, targeting all bacterial species were detected using the molecular beacon; 6-FAM-5'-CCGAGCTTAGTTGCCAT-CATTTAGTTGGGCACTCTAGCTCGG-3'-DABCYL (SEQ. ID. 20) (nucleotides 1113 to 1142 using *Streptococcus pneumonia* G54 as a reference) designed to detect all Gram-positive bacterial pathogens. The detection signals of the positive controls and the spiked blood samples recovered from blood pretreatment were presented in FIG. 19. This example demonstrates the efficiency of molecular beacon method to detect Gram-positive *S. pneumoniae* spiked in human whole blood with sensitivity in the range of 1-6 cells.

Example 3.3

Detection of Gram-Negative Bacteria Spiked in Human Whole Blood

Samples spiked with *E. coli* were prepared and processed as described above for RT-PCR assay. The one-step RT-PCR protocol used UB primer pair (UBF8 forward primer; 5'-CG-GCTAACTCCGTGCCAGCAG-3' (SEQ. ID. 12) and UBRs reverse primer; 5'-ATCTCTACGCATTTCACCGCTACAC-3') (SEQ. ID. 2) and GN1 primer pair (GN1F forward primer; 5'-GTTACCCGCAGAAGAAGCAC-3' (SEQ. ID. 13) and GN1R reverse primer; 5'-ACCTGAGCGTCAGTCTTCGT-3' (SEQ. ID. 14) targeting all Gram-negative bacterial species. The 16S rRNA gene fragment of 203 base pairs at a hypervariable region of all bacterial species (nucleotides 504 to 707 using *Escherichia coli* O104:H4 str. 2011C-3493 as a reference) was amplified by universal bacterial UB primer pair and the 16S rRNA gene fragment of 278 bases pair in a hypervariable region of all Gram-negative bacterial species (nucleotide 475 to 753 using *Escherichia coli* NR 024570.1 as reference) was amplified by Gram-negative specific GN1 primer pair.

Figure 20:
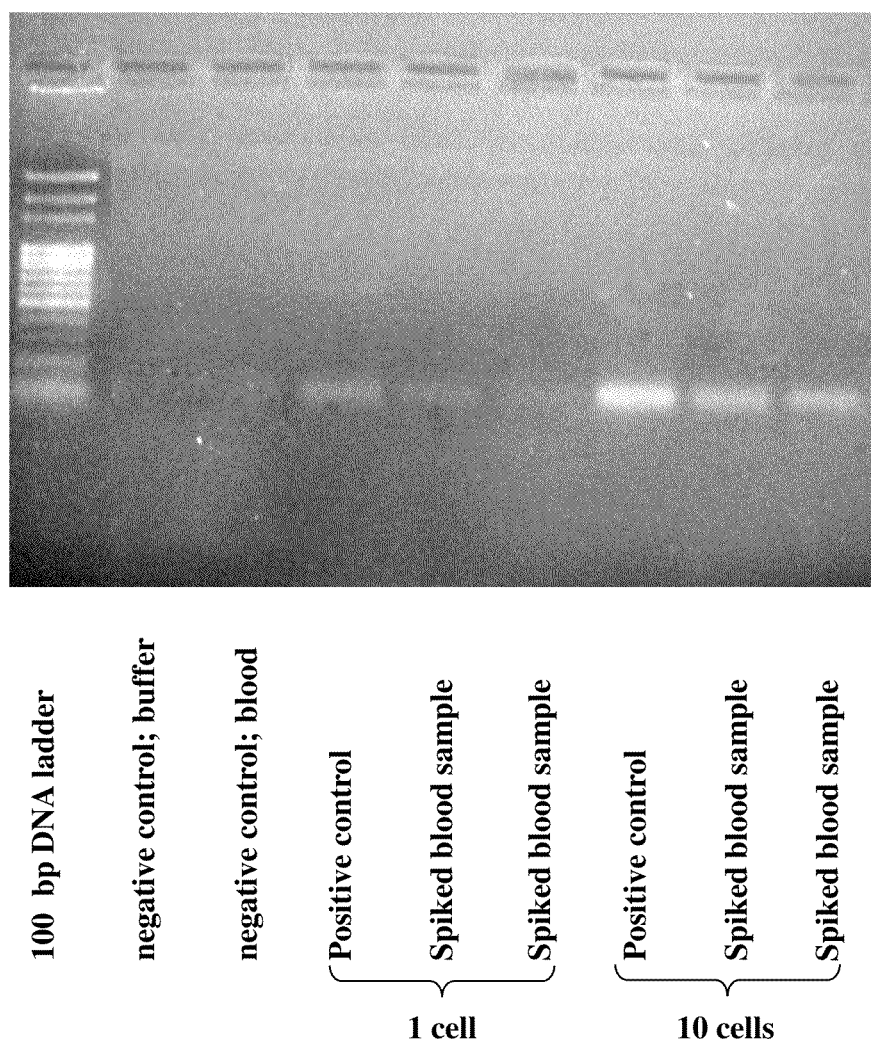
FIG. 20 demonstrates detection limit of *Escherichia coli* in blood samples. Reverse transcription PCR amplified product of the 16S rRNA fragment of *E. coli* was visualized after resolving on agarose gel electrophoresis, showing the detection of 1 and 10 *E. coli* cells.

The resulting amplified product using GN1 primer pair, targeting all Gram-negative bacterial species was resolved by gel electrophoresis and the amplified fragment of 16S rRNA was observed in FIG. 20. This example demonstrates the detection of Gram-negative *E. coli* bacteria in blood with sensitivity in the range of 1-6 cells.

The Gram-positive specific nucleotide sequences within the amplified product using UB universal bacterial primer pair, targeting all bacterial species were detected using the molecular beacon; 6-FAM-5'-CCGAGCGGTGCAAGCGT-TAATCGGAATTACTGGGCGCTCGG-3'-DABCYL (SEQ. ID. 5) (nucleotides 541-569 using *Escherichia coli* O104:H4 str. 2011C-3493 as a reference) designed to detect all Gram-negative bacterial pathogens. The detection signals of the spiking controls and the spiked blood samples recovered from blood pretreatment were presented in FIG. 21. This example demonstrates the efficiency of molecular beacon method to detect Gram negative *E. coli* spiked in human whole blood with sensitivity in the range of 1-6 cells.

Example 4

Repeatability of Detection Method as Measured Using Real-Time RT-PCR

This example demonstrates the repeatability of the detection of microbial cells in 1 mL of human whole blood sample within a total run-time of 30 minutes. Although the end goal is a multiplexed detection scheme, the present example is the detection of a single species.

Five different species each of Gram-positive, Gram-negative and fungal microbial cells described in FIG. 22, the representatives of the example panels in FIGS. 9 and 10, were tested. Sixty cells of each species were spiked into 1 mL of blood. The blood samples were then pre-treated to obtain 300 µL of pretreated samples in filter-sterilized 0.8 mM phosphate buffer and designated as spiked blood samples. Sixty cells of each species were added into 300 µL of filter-sterilized 0.8 mM phosphate buffer and used as respective positive controls. The blood of 1 mL volume without spiking with microbial cells also was pre-treated to obtain 300 µL of a pretreated sample in filter-sterilized 0.8 mM phosphate buffer and designated as a negative control (blood). Each sample and control of 70 µL was electrically lysed and RT-PCR assay was performed on 5.5 µL of each lysate, which is equivalent to detection at a single cell level. RT-PCR reaction of 20 µL volume was prepared by mixing 5.5 µL of sample, 10 µl of 2×PCR reaction mix (GoTaq Colourless, Promega), 1.5 µL of reverse transcriptase (GoScript, Promega), 0.5 µl of forward primer (10 µM), 0.5 µl of reverse primer (10 µM) and 2 µl of SYTO-9 (100 nM). One-step real-time RT-PCR was performed by reverse transcription at 55° C. for 5 min, inactivation of reverse transcription at 95° C. for 2 min, followed by 30 cycles of cDNA amplification at 95° C. for 3 sec, 59° C. for 3 sec, and 72° C. for 3 sec in Eco real time PCR system (Illumina) using a double stranded DNA binding fluorescent dye, SYTO-9. The primers used for RT-PCR to detect Gram-positive bacteria, Gram-negative bacteria and fungi are presented in FIG. 23.

The duration of sample pretreatment process was 6 minutes. The electrical lysis of samples or controls in steps of 10 µL/10s took place in 1 minute. The RT-PCR assay with real time detection was under 20 minutes. Therefore, the total run-time for the detection of microbial cells in 1 mL of raw human whole blood was 27 minutes.

Figure 24:
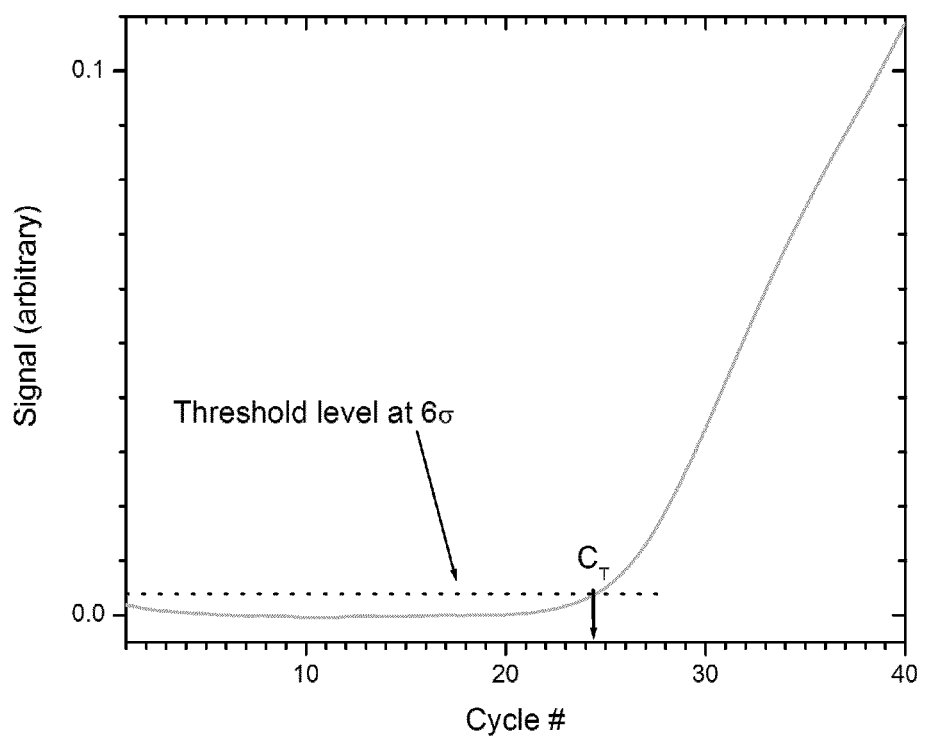
FIG. 24 shows the fluorescence signal measured during a typical real time PCR assay.

The detectability criterion was defined as the following. The RT-PCR fluorescence signal versus cycle number for the case of a single *Enterococcus faecalis* cell in human whole blood is presented in FIG. 24. The standard deviation of the signal over the first 10 cycles, where the signal is predominately background noise, is calculated and indicated as a large dashed line in FIG. 24. A threshold signal level is decided to be 6σ. The cycle number where the recorded signal exceeds the threshold level is defined as $C_T$. If the $C_T$ value of a sample differs by more than 5 cycles (a signal to noise ratio of over 32) from the $C_T$ value of the corresponding negative control blood sample running in parallel with the sample, the detection is considered to be unambiguous.

Example 4.1

Rapid Detection of Gram-Positive Bacteria in Raw Human Whole Blood

Five pathogenic species were tested: EF (*Enterococcus faecalis*), SS (*Streptococcus sanguis*), SP (*Streptococcus pneumonia*), SA (*Staphylococcus aureus*), and SPy (*Streptococcus pyogenes*). Spiked blood samples, and positive and negative controls were prepared and subjected to electrical lysis as described above. The RT-PCR protocol used GPF8 forward primer; 5'-GCTCGTGTCGTGAGATGTTGGG-3' (SEQ. ID. 21) and GPR8 reverse primer, 5'-CAGGTCAT-AAGGGGCATGATGAT-3' (SEQ. ID. 22). The 16S rRNA gene fragment of 151 base pairs at a hypervariable region of all Gram-positive bacterial species (nucleotides 1069 to 1220 using *Staphylococcus* sp. LS255 as a reference) was amplified.

Figure 25:
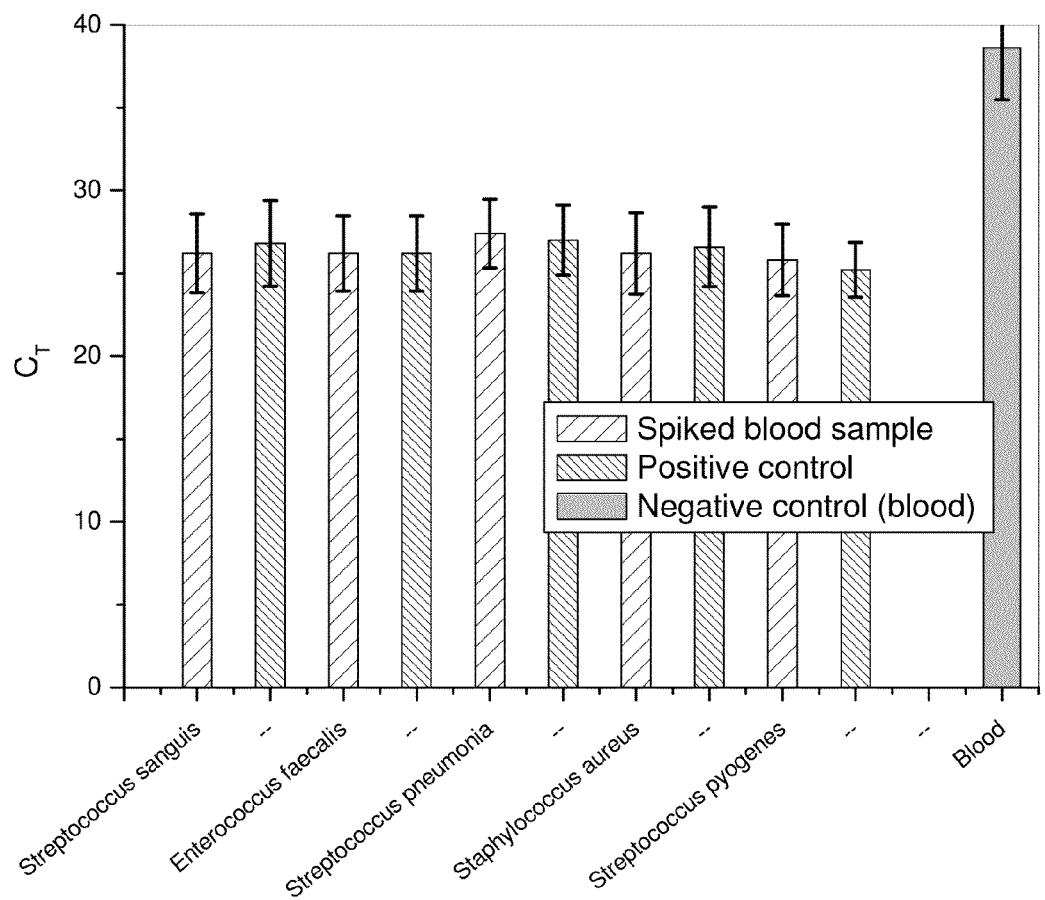
FIG. 25 shows the $C_T$ values for the detection of single cell of different Gram-positive bacterial cells in blood samples.

The resulting $C_T$ values for different species over five independent runs are presented in FIG. 25. The detection limit criterion as described above was satisfied for all Gram-positive species.

Example 4.2

Rapid Detection of Gram-Negative Bacteria in Raw Human Whole Blood

Figure 26:
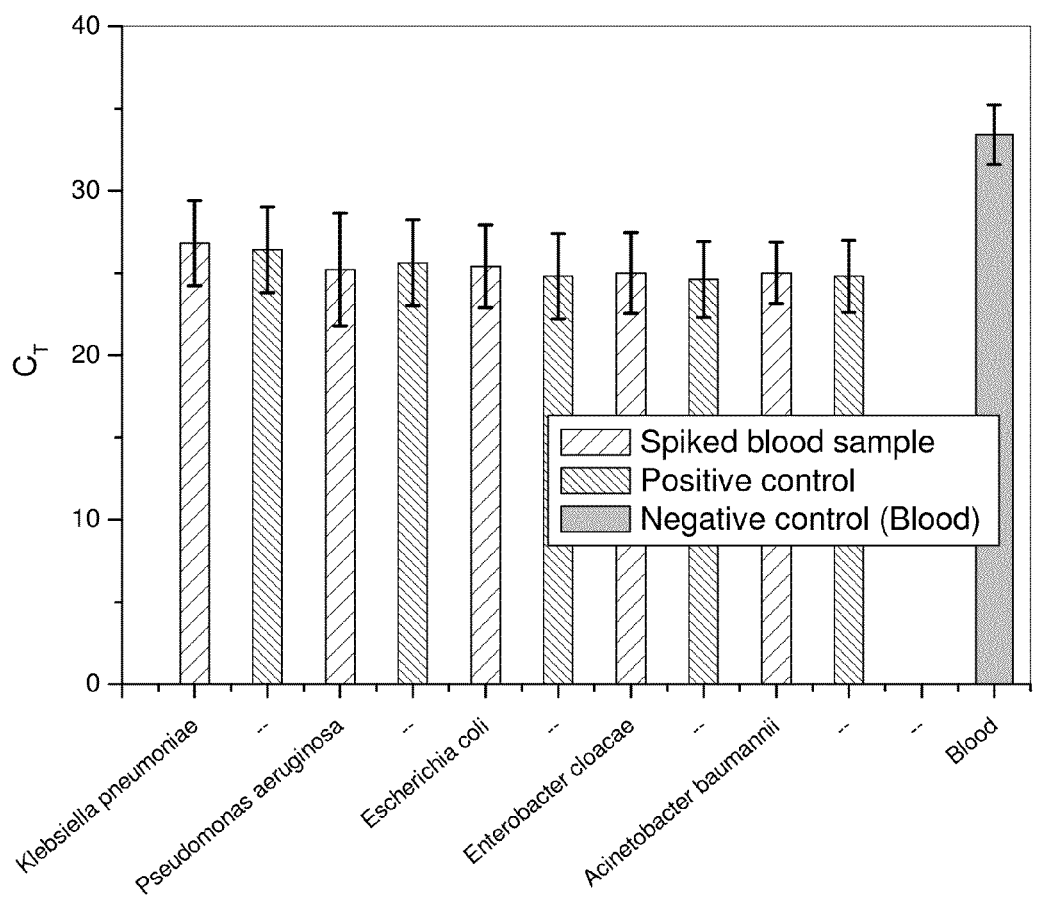
FIG. 26 shows the $C_T$ values for the detection of single cell of different Gram-negative bacterial cells in blood samples.
Figure 27:
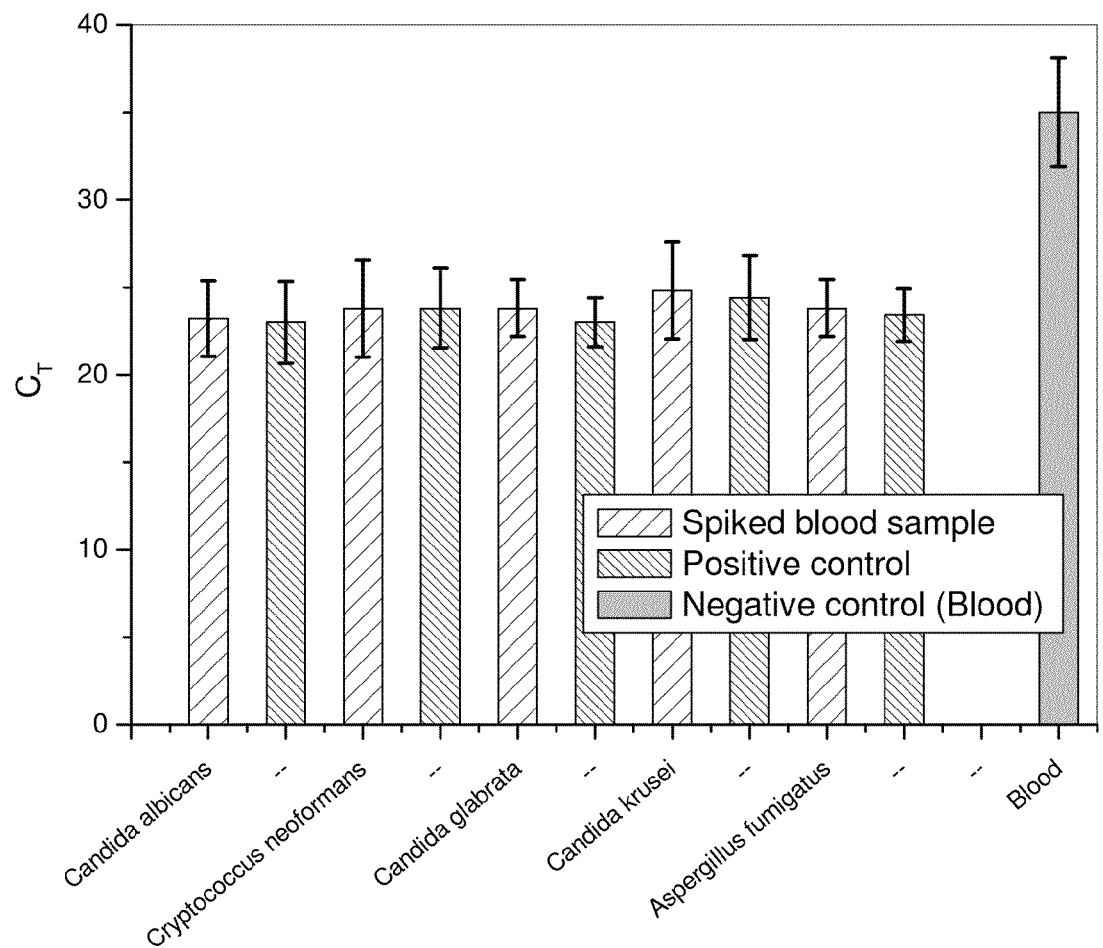
FIG. 27 shows the $C_T$ values for the detection of single cell of different fungal cells in blood samples.

Five pathogenic species were tested: KP (*Klebsiella pneumoniae*), PA (*Pseudomonas aeruginosa*), EC (*Escherichia coli*), ECL (*Enterobacter cloacae*), and AB (*Acinetobacter baumannii*). Spiked blood samples, and positive and negative controls were prepared and subjected to electrical lysis as described above. The RT-PCR protocol used GNF8 forward primer; 5'-GTTACCCGCAGAAGAAGCACCG-3' (SEQ. ID. 23) and GNR8 reverse primer, 5'-ATGCAGTTCCCAG-GTTGAGCC-3' (SEQ. ID. 24). The 16S rRNA gene fragment of 151 base pairs at a hypervariable region of all Gram-negative bacterial species (nucleotides 484 to 635 using *Escherichia coli* lal1 as a reference) was amplified. The resulting $C_T$ values for different species over five independent runs are presented in FIG. 26. The detection limit criterion as described above was satisfied for all Gram-negative species.

Example 4.3

Rapid Detection of Fungi in Raw Human Whole Blood

Five pathogenic species were tested: CA (*Candida albicans*), CrN (*Cryptococcus neoformans*), CG (*Candida glabrata*), CK (*Candida krusei*), and AF (*Aspergillus fumigatus*). Spiked blood samples, and positive and negative controls were prepared and subjected to electrical lysis as described above. The RT-PCR protocol used UFF2 forward primer; 5'-ACGGGGAGGTAGTGACAATAAAT-3'(SEQ. ID. 9) and UFR2 reverse primer, 5'-CCCAAGGTTCAAC-TACGAGCTT-3' (SEQ. ID. 10). The 18S rRNA gene fragment of 190 base pairs at a hypervariable region of all fungal species (nucleotide 434 to 624 using *Candida albicans* AB013586 as a reference) was amplified. The resulting $C_T$ values for different species over five independent runs are presented in FIG. 29. The detection limit criterion as described above was satisfied for all fungal species.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of extracting microbial cells from a whole blood sample in a pretreatment vessel,
the pretreatment vessel comprising a pretreatment mixture, the pretreatment mixture comprising:
a blood cell lysis reagent; and
a hydrophobic cushioning liquid having a density greater than that of the whole blood sample and the blood cell lysis reagent;
the method comprising:
adding a whole blood sample to the pretreatment vessel;
agitating the contents of the pretreatment vessel such that blood cells in the sample are selectively lysed by the blood cell lysis reagent;
centrifuging the pretreatment vessel such that the cushioning liquid forms a liquid interface below a supernatant, wherein microbial cells within from the whole blood sample are removed from suspension and collected adjacent to the liquid interface;
withdrawing a substantial quantity of the supernatant without extracting the collected microbial cells;
agitating the contents of the pretreatment vessel and allowing the cushioning liquid to re-establish the liquid interface below a microbial cell suspension containing the microbial cells; and
extracting a least a substantial portion of the microbial cell suspension without extracting a substantial portion of the cushioning liquid.

2. The method according to claim 1 wherein the volume of cushioning liquid is between approximately 0.1% and 10% of the vessel volume.

3. The method according to claim 1 wherein prior to agitating the contents of the pretreatment vessel and allowing the cushioning liquid to reestablish the liquid interface below the microbial cell suspension containing the microbial cells, the following washing steps are performed:
adding a volume of wash buffer to the pretreatment vessel;
agitating the contents of the pretreatment vessel;
centrifuging the pretreatment vessel such that the cushioning liquid forms a liquid interface below a supernatant, and such that microbial cells are transported to and collected at the liquid interface; and withdrawing a substantial quantity of the supernatant without extracting the collected microbial cells.

4. The method according to claim 3 further comprising performing the washing steps one or more additional times.

5. The method according to claim 1 wherein after centrifugation, the liquid interface is formed on a side portion of the pretreatment vessel, wherein the method further comprises re-orienting the pretreatment vessel such that the liquid interface is substantially horizontal, and wherein reorientation of the pretreatment vessel is performed such that a substantial quantity of the microbial cells remain collected at the liquid interface.

6. The method according to claim 1 wherein the blood cell lysis reagent is an aqueous solution containing saponin in an amount ranging between approximately 1.5 and 80 milligram per milliliter of whole blood and blood cell lysis reagent mixture.

7. The method according to claim 1 wherein the blood cell lysis reagent further contains sodium polyanetholesulfonate in an amount ranging between approximately 0.5 and 20 mg, per milliliter of whole blood and blood cell lysis reagent mixture.

8. The method according to claim 1 wherein the blood cell lysis reagent further comprises contains an antifoaming agent.

9. The method according to claim 8 wherein the antifoaming agent is poly(propylene glycol).

10. The method according to claim 1 further comprising:
lysing the microbial cells within the extracted microbial cell suspension to obtain a lysate; and
performing at least one assay to detect at least one analyte that may be present in the lysate.

11. The method according to claim 10 wherein the step of lysing the microbial cells is performed electrically.

12. The method according to claim 11 wherein the electrical lysis is performed according to the steps of:
providing a microfluidic device comprising:
a fluidic channel having an upper channel surface, a lower channel surface, a side wall, and a thickness on a submillimeter scale;
an upper electrode on the upper channel surface; and
a lower electrode on the lower channel surface;
wherein the channel is adapted to support flash heating of the extracted microbial cell suspension under the application of voltage pulses to the electrodes;
flowing the extracted microbial cell suspension into the channel; and
applying a series of bipolar voltage pulses between the upper electrode and the lower electrode, wherein an amplitude, pulse width, and duration of the voltage pulses are sufficient to flash heat the extracted microbial cell suspension and irreversibly electroporate the microbial cells, thereby releasing macromolecules from the microbial cells.

13. The method according to claim 10 wherein at least one of the assays is performed by polymerase chain reaction.

14. The method according to claim 10 wherein at least one of the assays is performed, at least in part, by reverse transcription polymerase chain reaction.

15. The method according to claim 10 wherein at least one of the analytes is rRNA.

16. The method according to claim 1 wherein the microbial cells are bacterial and/or fungal cells.

* * * * *

SEQUENCE LISTING

<160> NUMBER OF SEQ ID NOS: 24

<210> SEQ ID NO 1
<211> LENGTH: 21
<212> TYPE: DNA
<213> ORGANISM: Artificial
<220> FEATURE:
<223> OTHER INFORMATION: Pan bacterial primer

<400> SEQUENCE: 1
cggctaactc cgtgccagca g         21

<210> SEQ ID NO 2
<211> LENGTH: 25
<212> TYPE: DNA
<213> ORGANISM: Artificial
<220> FEATURE:
<223> OTHER INFORMATION: Pan bacterial primer

<400> SEQUENCE: 2
atctctacgc atttcaccgc tacac         25

<210> SEQ ID NO 3
<211> LENGTH: 23
<212> TYPE: DNA
<213> ORGANISM: Artificial
<220> FEATURE:
<223> OTHER INFORMATION: Pan fungal primer

<400> SEQUENCE: 3 aggggaggt agtgacaata aat         23

<210> SEQ ID NO 4
<211> LENGTH: 20
<212> TYPE: DNA
<213> ORGANISM: Artificial
<220> FEATURE:
<223> OTHER INFORMATION: Pan fungal primer

<400> SEQUENCE: 4
caaagttcaa ctacgagctt         20

<210> SEQ ID NO 5
<211> LENGTH: 41
<212> TYPE: DNA
<213> ORGANISM: Artificial
<220> FEATURE:
<223> OTHER INFORMATION: Pan gram negative bacterial probe

<400> SEQUENCE: 5
ccgagcggtg caagcgttaa tcggaattac tgggcgctcg g         41

<210> SEQ ID NO 6
<211> LENGTH: 38
<212> TYPE: DNA
<213> ORGANISM: Artificial
<220> FEATURE:
<223> OTHER INFORMATION: Pan fungal probe

<400> SEQUENCE: 6
ccgagctctg gtgccagcag ccgcggtaat cgctcgg         38

<210> SEQ ID NO 7
<211> LENGTH: 19
<212> TYPE: DNA
<213> ORGANISM: Artificial

```
<220> FEATURE:
<223> OTHER INFORMATION: Pan bacterial primer

<400> SEQUENCE: 7
agagtttgat cctggctag                                                19

<210> SEQ ID NO 8
<211> LENGTH: 20
<212> TYPE: DNA
<213> ORGANISM: Artificial
<220> FEATURE:
<223> OTHER INFORMATION: Pan bacterial primer

<400> SEQUENCE: 8
taaggttctt cgcgttgctt                                               20

<210> SEQ ID NO 9
<211> LENGTH: 23
<212> TYPE: DNA
<213> ORGANISM: Artificial
<220> FEATURE:
<223> OTHER INFORMATION: Pan fungal primer

<400> SEQUENCE: 9
acggggaggt agtgacaata aat                                           23

<210> SEQ ID NO 10
<211> LENGTH: 22
<212> TYPE: DNA
<213> ORGANISM: Artificial
<220> FEATURE:
<223> OTHER INFORMATION: Pan fungal primer

<400> SEQUENCE: 10
cccaaggttc aactacgagc tt                                            22

<210> SEQ ID NO 11
<211> LENGTH: 20
<212> TYPE: DNA
<213> ORGANISM: Artificial
<220> FEATURE:
<223> OTHER INFORMATION: Pan gram positive bacterial primer

<400> SEQUENCE: 11
atgcatagcc gacctgagag                                               20

<210> SEQ ID NO 12
<211> LENGTH: 19
<212> TYPE: DNA
<213> ORGANISM: Artificial
<220> FEATURE:
<223> OTHER INFORMATION: Pan gram positive bacterial primer

<400> SEQUENCE: 12
agttagccgt ssctttctg                                                19

<210> SEQ ID NO 13
<211> LENGTH: 20
<212> TYPE: DNA
<213> ORGANISM: Artificial
<220> FEATURE:
<223> OTHER INFORMATION: Pan gram negative bacterial primer

<400> SEQUENCE: 13
gttacccgca gaagaagcac                                               20
```

<210> SEQ ID NO 14
<211> LENGTH: 20
<212> TYPE: DNA
<213> ORGANISM: Artificial
<220> FEATURE:
<223> OTHER INFORMATION: Pan gram negative bacterial primer

<400> SEQUENCE: 14
acctgagcgt cagtcttcgt                                               20

<210> SEQ ID NO 15
<211> LENGTH: 22
<212> TYPE: DNA
<213> ORGANISM: Artificial
<220> FEATURE:
<223> OTHER INFORMATION: Pan fungal primer

<400> SEQUENCE: 15
aacgaaagtt agggatcga ag                                             22

<210> SEQ ID NO 16
<211> LENGTH: 21
<212> TYPE: DNA
<213> ORGANISM: Artificial
<220> FEATURE:
<223> OTHER INFORMATION: Pan fungal primer

<400> SEQUENCE: 16
ctttaagttt cagccttgcg a                                             21

<210> SEQ ID NO 17
<211> LENGTH: 33
<212> TYPE: DNA
<213> ORGANISM: Artificial
<220> FEATURE:
<223> OTHER INFORMATION: Pan fungal probe

<400> SEQUENCE: 17
ccgagccgta gtcttaacca taaactatgc gct                                33

<210> SEQ ID NO 18
<211> LENGTH: 21
<212> TYPE: DNA
<213> ORGANISM: Artificial
<220> FEATURE:
<223> OTHER INFORMATION: Pan bacterial primer

<400> SEQUENCE: 18
gacaggtggt gcatggttgt c                                             21

<210> SEQ ID NO 19
<211> LENGTH: 20
<212> TYPE: DNA
<213> ORGANISM: Artificial
<220> FEATURE:
<223> OTHER INFORMATION: Pan bacterial primer

<400> SEQUENCE: 19
acgtcatccc caccttcctc                                               20

<210> SEQ ID NO 20
<211> LENGTH: 42
<212> TYPE: DNA
<213> ORGANISM: Artificial
<220> FEATURE:
<223> OTHER INFORMATION: Pan gram positive bacterial probe

```
<400> SEQUENCE: 20
ccgagcttag ttgccatcat ttagttgggc actctagctc gg                          42

<210> SEQ ID NO 21
<211> LENGTH: 22
<212> TYPE: DNA
<213> ORGANISM: Artificial
<220> FEATURE:
<223> OTHER INFORMATION: Pan gram positive bacterial primer

<400> SEQUENCE: 21
gctcgtgtcg tgagatgttg gg                                                22

<210> SEQ ID NO 22
<211> LENGTH: 23
<212> TYPE: DNA
<213> ORGANISM: Artificial
<220> FEATURE:
<223> OTHER INFORMATION: Pan gram positive bacterial primer

<400> SEQUENCE: 22
caggtcataa ggggcatgat gat                                               23

<210> SEQ ID NO 23
<211> LENGTH: 22
<212> TYPE: DNA
<213> ORGANISM: Artificial
<220> FEATURE:
<223> OTHER INFORMATION: Pan gram negative bacterial primer

<400> SEQUENCE: 23
gttacccgca gaagaagcac cg                                                22

<210> SEQ ID NO 24
<211> LENGTH: 21
<212> TYPE: DNA
<213> ORGANISM: Artificial
<220> FEATURE:
<223> OTHER INFORMATION: Pan gram negative bacterial primer

<400> SEQUENCE: 24
atgcagttcc caggttgagc c                                                 21
```